US011061028B2

(12) United States Patent
Lukinova et al.

(10) Patent No.: US 11,061,028 B2
(45) Date of Patent: Jul. 13, 2021

(54) COMPOSITIONS AND METHODS FOR THE DIAGNOSIS OF LYME DISEASE

(71) Applicant: Defined Diagnostics, LLC, Rockville, MD (US)

(72) Inventors: Nina Lukinova, Germantown, MD (US); Xiaoling Song, Frederick, MD (US); Paul Francis Macomber, Herndon, VA (US); Jill Ann White, Taneytown, MD (US)

(73) Assignee: Defined Diagnostics, LLC, Rockville, MD (US)

( * ) Notice: Subject to any disclaimer, the term of this patent is extended or adjusted under 35 U.S.C. 154(b) by 99 days.

(21) Appl. No.: 15/514,264

(22) PCT Filed: Sep. 23, 2015

(86) PCT No.: PCT/US2015/051665
§ 371 (c)(1),
(2) Date: Mar. 24, 2017

(87) PCT Pub. No.: WO2016/049148
PCT Pub. Date: Mar. 31, 2016

(65) Prior Publication Data

US 2018/0149648 A1 May 31, 2018

Related U.S. Application Data

(60) Provisional application No. 62/054,671, filed on Sep. 24, 2014.

(51) Int. Cl.

| | |
|---|---|
| ***A61K 39/00*** | (2006.01) |
| ***A61K 39/40*** | (2006.01) |
| ***A61K 39/395*** | (2006.01) |
| ***G01N 33/569*** | (2006.01) |
| ***G01N 33/68*** | (2006.01) |
| ***C12Q 1/04*** | (2006.01) |

(52) U.S. Cl.
CPC ......... *G01N 33/56911* (2013.01); *C12Q 1/04* (2013.01); *G01N 33/6893* (2013.01); *G01N 2333/20* (2013.01); *G01N 2458/00* (2013.01); *G01N 2469/20* (2013.01); *G01N 2800/24* (2013.01); *Y02A 50/30* (2018.01)

(58) Field of Classification Search
CPC .. A61K 39/00; A61K 39/0225; A61K 39/395; A61K 39/40
USPC ......... 424/130.1, 164.1, 184.1, 185.1, 192.1, 424/234.1; 435/4, 7.1, 7.2, 7.3
See application file for complete search history.

(56) References Cited

U.S. PATENT DOCUMENTS

| | | | |
|---|---|---|---|
| 5,618,533 A | 4/1997 | Flavell et al. | |
| 5,977,339 A | 11/1999 | Lefebyre et al. | |
| 6,210,676 B1 | 4/2001 | Callister et al. | |
| 6,437,116 B1 | 8/2002 | Norris et al. | |
| 6,475,492 B1 | 11/2002 | Philipp et al. | |
| 6,509,017 B1 | 1/2003 | Bergstrom et al. | |
| 6,719,983 B2 | 4/2004 | Norris et al. | |
| 6,740,744 B2 | 5/2004 | Norris et al. | |
| 7,135,176 B2 | 11/2006 | Norris et al. | |
| 7,785,597 B2 | 8/2010 | Norris et al. | |
| 7,887,815 B2 | 2/2011 | Dattwyler et al. | |
| 8,129,165 B2 | 3/2012 | Lundberg et al. | |
| 8,247,181 B2 | 8/2012 | Barbour et al. | |
| 8,303,961 B2 | 11/2012 | Lundberg et al. | |
| 8,338,566 B2 | 12/2012 | Pal et al. | |
| 8,926,989 B2 | 1/2015 | Burbelo et al. | |
| 2003/0059894 A1 | 3/2003 | Phillip | |
| 2006/0034862 A1 | 2/2006 | Lahdenne et al. | |
| 2010/0150964 A1 | 6/2010 | Komorowski et al. | |
| 2010/0278866 A1 | 11/2010 | Barbour et al. | |
| 2010/0292096 A1 | 11/2010 | Luft et al. | |
| 2011/0105355 A1 | 5/2011 | Luft et al. | |
| 2011/0136155 A1* | 6/2011 | Mehra .............. | G01N 33/56911 435/7.92 |
| 2011/0294147 A1 | 12/2011 | Burbelo et al. | |
| 2012/0142023 A1 | 6/2012 | Ascoli et al. | |
| 2013/0164759 A1 | 6/2013 | Burbelo et al. | |
| 2013/0210651 A1 | 8/2013 | Barbour et al. | |
| 2014/0364332 A1 | 12/2014 | Mehra et al. | |

FOREIGN PATENT DOCUMENTS

| | | |
|---|---|---|
| WO | WO 199858943 | 12/1998 |
| WO | WO 2009033163 | 3/2009 |
| WO | WO 2009131665 | 10/2009 |
| WO | WO 2011112805 | 9/2011 |

OTHER PUBLICATIONS

The International Search Report and the Written Opinion for International Application No. PCT/US2015/051665, dated Feb. 5, 2016.

Baum et al., “Experimental Infections of the Reservoir Species *Peromyscus leucopus* with Diverse Strains of Borrelia burgdorferi, a Lyme Disease Agent,” mBio 3(6):e00434-12.doi:10.1128/mBio.00434-12 (2012).

Coleman et al., “BBK07, a Dominant In Vivo Antigen of Borrelia burgdorferi, Is a Potential Marker for Serodiagnosis of Lyme Disease,” Clin. Vac. Immuno., vol. 16, No. 11, p. 1569-1575 (Nov. 2009).

(Continued)

*Primary Examiner* — Rodney P Swartz
(74) *Attorney, Agent, or Firm* — Lewis J. Kreisler

(57) ABSTRACT

This disclosure provides antigen compositions useful for diagnosing Lyme disease and for detecting antibodies that bind to *Borrelia* antigens. The antigenic compositions comprise a mixture of hybrid peptides and *Borrelia* proteins. This disclosure also provides devices, methods, and kits that are useful for diagnosing Lyme disease and for detecting anti-*Borrelia* antibodies in a sample to aid in the diagnosis of Lyme disease.

11 Claims, 13 Drawing Sheets

Specification includes a Sequence Listing.

(56) References Cited

OTHER PUBLICATIONS

Coleman et al., "BBK07 Immunodominant Peptides as Serodiagnostic Markers of Lyme Disease," Clin. Vac. Immuno., vol. 18, No. 3, p. 406-413 (Mar. 2011).
Heikkila et al., "Species-Specific Serodiagnosis of Lyme Arthritis and Neuroborreliosis Due to Borrelia burgdorferi Sensu Stricto, B. afzelii, and B. garinii by Using Decorin Binding Protein A," J Clin. Microbiol., vol. 40, No. 2, p. 453-460 (Feb. 2002).
Heikkila et al., "Cloning of the gene encoding the decorin-binding protein B (DbpB) in Borrelia burgdorferi sensu lato and characterisation of the antibody responses to DbpB in Lyme borreliosis," J Med. Microbiol., vol. 51, p. 641-648 (Mar. 2002).
Namba et al., "Highly Sensitive Electrochemiluminescence Immunoassay Using the Ruthenium Chelate-Labeled Antibody Bound on the Magnetic Micro Beads," Anal. Sci., vol. 15, No. 11, p. 1087-1093 (Nov. 1999).
Aguero-Rosenfeld et al., "Diagnosis of lyme borreliosis," Clin. Microbiol. Rev., vol. 18, pp. 484-509 (2005).
Alarcon-Chaidez et al., "Confirmation of tick bite by detection of antibody to Ixodes calreticulin salivary protein," Clin. Vaccine Immunol., vol. 13, No. 11, pp. 1217-1222 (2006).
Andrade et al., "Biomarkers for exposure to sand flies bites as tools to aid control of leishmaniasis," Front Immunol. vol. 3, No. 121 (2012); (Epub 2012).
Anguita et al., "Borrelia burgdorferi gene expression in vivo and spirochete pathogenicity," Infect. Immun., vol. 68, No. 3, pp. 1222-1230 (2000).
Bacon et al., "Serodiagnosis of Lyme Disease by Kinetic Enzymatic-Linked Immunosorbent Assay Using Recombinant V1sE1 or Peptide Antigens of Borrelia burgdorfei Compared with 2-Tiered Testing Using Whole-Cell Lysates," J. Infec. Dis., vol. 187, No. 15, pp. 1187-1899 (2003).
Barbour, A.G., "Immunochemical analysis of Lyme disease spirochetes," Yale J. Biol. Med., vol. 57, pp. 581-586 (1984).
Barbour, A.G., "Isolation and cultivation of Lyme disease spirochetes," Yale J. Biol. Med., vol. 57, pp. 521-525 (1984).
Barbour, A.G., "Plasmid analysis of Borrelia burgdorferi, the Lyme disease agent," J. Clin. Microbiol., vol. 26, pp. 475-478 (1988).
Barbour et al., "Antibodies of patients with Lyme disease to components of the Ixodes dammini spirochete," J. Clin. Investig., vol. 72, pp. 504-515 (1983).
Barbour et al., "Lyme disease spirochetes and Ixodid tick spirochetes share a common surface antigenic determinant defined by a monoclonal antibody," Infect. Immun., vol. 41, pp. 795-804 (1983).
Barbour et al., "A Borrelia-specific monoclonal antibody binds to a flagellar epitope," Infect. Immun., vol. 52, pp. 549-554 (1986).
Barbour et al., "A Genome-Wide Proteome Array Reveals a Limited Set of Immunogens in Natural Infections of Humans and White-Footed Mice with Borrelia Burgdorferi," Infection and Immunity, vol. 76, No. 8, pp. 3374-3389 (2008).
Brinkman et al., "Reactivity of antibodies from syphilis patients to a protein array representing the Treponema pallidum proteome," J. Clin. Microbiol., vol. 44, pp. 888-891 (2006).
Brissette et al., "Borrelia burgdorferi RevA Antigen Binds Host Fibronectin," Infect. Immun., vol. 77, No. 7, pp. 2802-2812 (2009).
Brissette et al., "The Borrelial Fibronectin-Binding Protein RevA Is an Early Antigen of Human Lyme Disease," Clin. Vaccine Immunol., vol. 17, No. 2, pp. 274-280 (2010).
Brisson et al., "ospC diversity in Borrelia burgdorferi: different hosts are different niches," Genetics, vol. 168, pp. 713-722 (2004).
Brooks et al., "Global analysis of Borrelia burgdorferi genes regulated by mammalian host-specific signals," Infect. Immun., vol. 71, pp. 3371-3383 (2003).
Bunikis et al., "Surface exposure and species specificity of an immunoreactive domain of a 66-kilodalton outer membrane protein (P66) of the Borrelia spp. that cause Lyme disease," Infect. Immun., vol. 64, pp. 5111-5116 (1996).
Bunikis et al., "A surface-exposed region of a novel outer membrane protein (P66) of Borrelia spp. is variable in size and sequence," J. Bacteriol., vol. 180, pp. 1618-1623 (1998).
Bunikis et al., "Laboratory testing for suspected Lyme Disease," Med. Clin. N. Am., vol. 86, pp. 311-340 (2002).
Bunikis et al., "Sequence typing reveals extensive strain diversity of the Lyme borreliosis agents Borrelia burgdorferi in North America and Borrelia afzelii in Europe," Microbiology, vol. 150, pp. 1741-1755 (2004).
Bunikis et al., "Borrelia burgdorferi infection in a natural population of Peromyscus leucopus mice: a longitudinal study in an area where Lyme borreliosis is highly endemic," J. Infect. Dis., vol. 189, pp. 1515-1523 (2004).
Burbelo et al., "Rapid Simple, Quantitative, and Highly Sensitive Antibody Detection for Lyme Disease," Clinical Vaccine Immunol., vol. 17, No. 6, pp. 904-909 (2010).
Burgdorfer et al., "Lyme disease—a tick-borne spirochetosis?," Science, vol. 216, pp. 1317-1319 (1982).
Cadavid et al., "Immunologic and genetic analyses of VmpA of a neurotropic strain of Borrelia turicatae," Infect. Immun., vol. 65, pp. 3352-3360 (1997).
Carroll et al., "Borrelia burgdorferi RevA antigen is a surface-exposed outer membrane protein whose expression is regulated in response to environmental temperature and pH," Infect. Immun., vol. 69, No. 9, pp. 5286-5293 (2001).
Casjens et al., "A bacterial genome in flux: the twelve linear and nine circular extrachromosomal DNAs in an infectious isolate of the Lyme disease spirochete Borrelia burgdorferi," Mol. Microbiol., vol. 35, pp. 490-516 (2000).
Cinco et al., "Evidence of Dbps (decorin binding proteins) among European strains of Borrelia burgdorferi sensu lato and in the immune response to LB patient sera," FEMS Microbiol. Lett., vol. 183, No. 1, pp. 111-114 (2000).
Clifton et al., "Regulation and expression of bba66 encoding an immunogenic infection-associated lipoprotein in Borrelia burgdorferi," Mol. Microbiol., vol. 61, No. 1, pp. 243-258 (2006).
Coleman et al., "Identification and characterization of an endoflagellar antigen of Borrelia burgdorferi," J. Clin. Invest., vol. 84, No. 1, pp. 322-330 (1989).
Coleman et al., "Proteome and antigen profiling of Coxiella burnetiid developmental forms," Infect. Immun., vol. 75, pp. 290-298 (2007).
Collins et al., "Immunoreactive epitopes on an expressed recombinant flagellar protein of Borrelia burgdorferi," Infect. Immun., vol. 59, No. 2, pp. 514-520 (1991).
Connolly et al., "Proteomic analysis of *Brucella abortus* cell envelope and identification of immunogenic candidate proteins for vaccine development," Proteomics, vol. 6, pp. 3767-3780 (2006).
Craft et al., "Antigens of Borrelia burgdorferi recognized during Lyme disease. Appearance of a new immunoglobulin M response and expansion of the immunoglobulin G response late in the illness," J. Clin. Investig., vol. 78, pp. 934-939 (1986).
Crother et al., "Temporal Analysis of the Antigenic Composition of Borrelia burgdorferi during Infection in Rabbit Skin," Infect. Immun., vol. 72, No. 9, pp. 5063-5072 (2004).
Crotty et al., "Cutting edge: long-term B cell memory in humans after smallpox Vaccination," J. Immunol., vol. 171, pp. 4969-4973 (2003).
Crowder et al., "Geneotypic Variation and Mixtures of Lyme Borrelia in Ixodes Ticks from North America and Europe," PLoS One, vol. 5, No. 5, p. e10650 (2010).
Dai et al., "Antibodies against a tick protein, Salp15, protect mice from the Lyme disease agent," Cell Host Microbe., vol. 6, No. 5, pp. 482-492 (2009).
Daily et al., "In vivo transcriptome of Plasmodium falciparum reveals overexpression of transcripts that encode surface proteins," J. Infect. Dis., vol. 191, pp. 1196-1203 (2005).
Das et al., "Characterization of a 30-kDa Borrelia burgdorferi substrate-binding protein homologue," Res. Microbiol., vol. 147, pp. 739-751 (1996).
Davies et al., "Profiling the humoral immune response to infection by using proteome microarrays: high-throughput vaccine and diagnostic antigen discovery," Proc. Natl. Acad. Sci. USA, vol. 102, pp. 547-552 (2005).

(56) References Cited

OTHER PUBLICATIONS

Davies et al., "Vaccinia virus H3L envelope protein is a major target of neutralizing antibodies in humans and elicits protection against lethal challenge in mice," J. Virol., vol. 79, pp. 11724-11733 (2005).
Davies et al., "Proteome-wide analysis of the serological response to vaccinia and smallpox," Proteomics, vol. 7, pp. 1678-1686 (2007).
De Silva et al., "Arthropod- and host-specific gene expression by Borrelia burgdorferi," J. Clin. Investig., vol. 99, pp. 377-379 (1997).
Dressler et al., "Western blotting in the serodiagnosis of Lyme disease," J. Infect. Dis., vol. 167, pp. 392-400 (1993).
Dykhuizen et al., "Borrelia burgdorferi is clonal: implications for taxonomy and vaccine development," Proc. Natl. Acad. Sci. U.S.A., vol. 90, No. 21, pp. 10163-10167 (1993).
Engstrom et al., "Immunoblot interpretation criteria for serodiagnosis of early Lyme disease," J. Clin. Microbiol., Vo. 33, pp. 419-427 (1995).
Eyles et al., "Immunodominant Francisella tularensis antigens identified using proteome microarray," Dstl. Proteomics, vol. 7, pp. 2172-2183 (2007).
Feng et al., "A 55-kilodalton antigen encoded by a gene on a Borrelia burgdorferi 49-kilobase plasmid is recognized by antibodies in sera from patients with Lyme disease," Infect. Immun., vol. 63, pp. 3459-3466 (1995).
Feng et al., "Humoral immunity to Borrelia burgdorferi N40 decorin binding proteins during infection of laboratory mice," Infect. Immun., vol. 66, No. 6, pp. 2827-2835 (1998).
Fikrig et al., "Borrelia burgdorferi P35 and P37 Proteins, Expressed In Vivo, Elicit Protective Immunity," Immunity, vol. 6, No. 5, pp. 531-539 (1997).
Fikrig et al., "Arthropod- and host-specific Borrelia burgdorferi bbk32 expression and the inhibition of spirochete transmission," J. Immunol., vol. 164, No. 10, pp. 5344-5351 (2000).
Fikrig et al., "Preferential presence of decorin-binding protein B (BBA25) and BBA50 antibodies in cerebrospinal fluid of patients with neurologic Lyme disease," J. Clin. Microbiol., vol. 42, No. 3, pp. 1243-1246 (2004).
Fischer et al., "Fibronectin binding protein BBK32 of the Lyme disease spirochete promotes bacterial attachment to glycosaminoglycans," Infect. Immun., vol. 74, No. 1, pp. 435-441 (2006).
Forgber, et al., "Mapping the antigenicity of the parasites in Leishmania donovani infection by proteome serology," PLoS One, vol., 1, p. e40 (2006).
Gardy et al., "PSORTb v. 2.0: expanded prediction of bacterial protein subcellular localization and insights gained from comparative proteome analysis," Bioinformatics, vol. 21, pp. 617-623 (2005).
Gassmann et al., "Nucleotide sequence of a gene encoding the Borrelia burgdorferi flagellin," Nucleic Acids Res., vol. 17, No. 9, p. 3590 (1989).
Gassmann et al., "Analysis of the Borrelia burgdorferi GeHo fla gene and antigenic characterization of its gene product," J. Bacteriol., vol. 173, No. 4, pp. 1452-1459 (1991).
Gautam et al., "Analysis of the determinants of bba64 (P35) gene expression in Borrelia burgdorferi using a gfp reporter," Microbiology, vol. 154, No. Pt 1, pp. 275-285 (2008).
Ge et al., "Identification of a large motility operon in Borrelia burgdorferi by semi-random PCR chromosome walking," Gene, vol. 189, No. 2, pp. 195-201 (1997).
Ge et al., "Molecular characterization of a large Borrelia burgdorferi motility operon which is initiated by a consensus sigma70 promoter," J. Bacteriol., vol. 179, No. 7, pp. 2289-2299 (1997).
Gilmore Jr. et al., "A monoclonal antibody generated by antigen inoculation via tick bite is reactive to the Borrelia burgdorferi Rev protein, a member of the 2.9 gene family locus, Infect," Immun., vol. 66, pp. 980-986 (1998).
Gilmore Jr. et al., "The Borrelia burgdorferi 37-kilodalton immunoblot band (P37) used in serodiagnosis of early Lyme disease is the flaA gene product," J. Clin. Microbiol., vol. 37, pp. 548-552 (1999).
Gilmore Jr. et al., "Analysis of Borrelia burgdorferi gene expression during life cycle phases of the tick vector Ixodes scapularis," Microbes Infect., vol. 3, No. 10, pp. 799-808 (2001).
Gilmore Jr. et al., "Borrelia burgdorferi expression of the bba64, bba65, bba66, and bba73 genes in tissues during persistent infection in mice," Microb. Pathog., vol. 45, Nos. 5-6, pp. 355-360 (2008); (Epub. 2008).
Glockner et al., "Comparative analysis of the Borrelia garinii genome," Nucleic Acids Res., vol. 32, pp. 6038-6046 (2004).
Goettner et al., "Improvement of Lyme Borreliosis Serodiagnosis by a Newly Developed Recombinant Immunoglobulin G (IgG) and IgM line Immunoblot Assay and Addition of VIsE and DbpA Homologues," J. Clin. Microbiol., vol. 43, pp. 3602-3609 (2005).
Gomes et al., "The immune response to sand fly salivary proteins and its influence on leishmania immunity," Front Immunol., vol. 3, p. 110 (2012); (Epub 2012).
Grab et al., "Fibronectin-binding activity in Borrelia burgdorferi," Biochim Biophys Acta., vol. 1407, No. 2, pp. 135-145 (1998).
Guo et al., "Adherence of Borrelia burgdorferi to the proteoglycan decorin," Infect. Immun., vol. 63, No. 9, pp. 3467-3472 (1995).
Guo et al., "Decorin-binding adhesins from Borrelia burgdorferi," Mol. Microbiol., vol. 30, No. 4, pp. 711-723 (1998).
Haas et al., "Immunoproteomics of Helicobacter pylori infection and relation to gastric disease," Proteomics, vol. 2, pp. 313-324 (2002).
Hansen et al., "Measurement of antibodies to the Borrelia burgdorferi flagellum improves serodiagnosis in Lyme disease," J. Clin. Microbiol., vol. 26, pp. 338-346 (1988).
Hauser et al., "Enzyme-linked immunosorbent assays with recombinant internal flagellin fragments derived from different species of Borrelia burgdorferi sensu lato for the serodiagnosis of Lyme neuroborreliosis," Med. Microbiol. Immunol., vol. 186, Nos. 2-3, pp. 145-151 (1997).
Heikkila et al., "Recombinant or Peptide Antigens in the Serology of Lyme Arthritis in Children," J. Infect. Dis., vol. 187, No. 12, pp. 1888-1894 (2003).
Hojgaard et al., "Molecular identification of Salp15, a key salivary gland protein in the transmission of lyme disease spirochetes, from Ixodes persulcatus and Ixodes pacificus (Acari: Ixodidae)," J. Med. Entomol., vol. 46, No. 6, pp. 1458-1463 (2009).
Hovius, J.W., "Spitting image: tick saliva assists the causative agent of Lyme disease in evading host skin's innate immune response," J. Invest. Dermatol., vol. 129, No. 10, pp. 2337-2339 (2009).
Howe et al., "A single recombinant plasmid expressing two major outer surface proteins of the Lyme disease spirochete," Science, vol. 227, pp. 645-646 (1985).
Jewett et al., "The critical role of the linear plasmid Ip 36 in the infectious cycle of Borrelia burgdorferi," Mol. Microbiol., vol. 64, pp. 1358-1374 (2007).
Johnson et al., "Serodiagnosis of Lyme disease: accuracy of a two-step approach using a flagella-based ELISA and immunoblotting," J. Infect. Dis., vol. 174, pp. 346-353 (1996).
Jwang et al., "The hook protein of Borrelia burgdorferi, encoded by the flgE gene, is serologically recognized in Lyme disease," Clin. Diagn. Lab. Immunol., vol. 2, No. 5, pp. 609-615 (1995).
Kaiser et al., "Analysis of the intrathecal immune response in neuroborreliosis to a sonicate antigen and three recombinant antigens of Borrelia burgdorferi sensu stricto," Eur. J. Clin. Microbiol. Infect. Dis., vol. 17, No. 3, pp. 159-166 (1998).
Kaiser et al., "Advantage of recombinant borrelial proteins for serodiagnosis of neuroborreliosis," J. Med. Microbiol., vol. 48, No. 1, pp. 5-10 (1999).
Kaiser et al., "Serodiagnosis of Neuroborreliosis: Comparison of Reliability of Three Confirmatory Assays," Infection, vol. 27, No. 3, pp. 177-182 (1999).
Kim et al., "BBK32, a fibronectin binding MSCRAMM from Borrelia burgdorferi, contains a disordered region that undergoes a conformational change on ligand binding," J. Biol. Chem., vol. 279, No. 40, pp. 41706-41714 (2004); (Epub. 2004).
Kornacki et al., "Lyme Disease-Causing Borrelia Species Encode Multiple Lipoproteins Homologous to Peptide-Binding Proteins of ABC-Type Transporters," Infect. Immun., vol. 66, No. 9, pp. 4115-4122 (1998).

(56) References Cited

OTHER PUBLICATIONS

Kowalczewska et al., "Identification of candidate antigen in Whipple's disease using a serological proteomic approach," Proteomics, vol. 6, pp. 3294-3305 (2006).
Lam et al., "A chromosomal Borrelia burgdorferi gene encodes a 22-kilodalton lipoprotein, P22, that is serologically recognized in Lyme disease," J. Clin. Microbiol., vol. 32, pp. 876-883 (1994).
Lawrenz et al., "Human antibody responses to VIsE antigenic variation protein of Borrelia burgdorferi," J. Clin. Microbiol., vol. 37, pp. 3997-4004 (1999).
Liang et al., "Sensitive and specific serodiagnosis of Lyme disease by enzyme-linked immunosorbent assay with a peptide based on an immunodominant conserved region of Borrelia burgdorferi vIsE," J. Clin. Microbiol., vol. 37, pp. 3990-3996 (1999).
Liang et al., "DNA microarray assessment of putative Borrelia burgdorferi lipoprotein genes," Infect. Immun., vol. 70, pp. 3300-3303 (2002).
Lu et al., "Generation and characterization of hybridoma antibodies for immunotherapy of tularemia," Immunol. Lett. vol. 112, pp. 92-103 (2007).
Luft et al., "Biochemical and immunological characterization of the surface proteins of Borrelia burgdorferi," Infect. Immun., vol. 57, No. 11, pp. 3637-3645 (1989).
Luft et al., "Immunologic and structural characterization of the dominant 66- to 73-kDa antigens of Borrelia burgdorferi," J. Immunol., vol. 146, pp. 2776-2782 (1991).
Magnarelli et al., "Use of recombinant antigens of Borrelia burgdorferi in serologic tests for diagnosis of lyme borreliosis," J. Clin. Microbiol., vol. 34, No. 2, pp. 237-240 (1996).
Marangoni et al., "Comparative evaluation of two enzyme linked immunosorbent assay methods and three Western Blot methods for the diagnosis of culture-confirmed early Lyme Borreliosis in Italy," New Microbiol., vol., 28, No. 1, pp. 37-43 (2005).
Maruskova et al., "Deletion of BBA64, BBA65, and BBA66 loci does not alter the infectivity of Borrelia burgdorferi in the murine model of Lyme disease," Infect. Immun., vol. 76, No. 11, pp. 5274-5284 (2008); (Epub. 2008).
Maruskova et al., "Role of the BBA64 locus of Borrelia burgdorferi in early stages of infectivity in a murine model of Lyme disease," Infect. Immun., vol. 76, No. 1, pp. 391-402 (2008); (Epub. 2007).
Mbow et al., "Borrelia burgdorferi-specific monoclonal antibodies derived from mice primed with Lyme disease spirochete-infected Ixodes scapularis ticks," Hybrid Hybridomics, vol. 21, No. 3, pp. 179-182 (2002).
McAtee et al., "Identification of potential diagnostic and vaccine candidates of Helicobacter pylori by "proteome" technologies," Helicobacter, vol. 3, pp. 163-169 (1998).
McKevitt et al., "Genome scale identification of Treponema pallidum antigens," Infect. Immun., vol. 73, pp. 4445-4450 (2005).
McNally et al., "Differential salivary gland transcript expression profile in Ixodes scapularis nymphs upon feeding or flavivirus infection," Ticks Tick Borne Dis., vol. 3, No. 1, pp. 18-26 (2012); (Epub 2012).
Meier et al., "Antigenic variation is associated with DNA rearrangements in a relapsing fever Borrelia," Cell, vol. 41, pp. 403-409 (1985).
Miller et al., "Borrelia burgdorferi B31 Erp proteins that are dominant immunoblot antigens of animals infected with isolate B31 are recognized by only a subset of human lyme disease patient sera," J. Clin. Microbiol., vol. 38, No. 4, pp. 1569-1574 (2000).
Miller et al., "Immunological and genetic characterization of Borrelia burgdorferi BapA and EppA proteins," Microbiology, vol. 149, pp. 1113-1125 (2003).
Motaleb et al., "A Novel Gene Inactivation System Reveals Altered Periplasmic Flagellar Orientation in a Borrelia burgdorferi fliL Mutant," J. Bacteriol., vol. 193, No. 13, pp. 3324-3331 (2011).
Nigrovic et al., "The Lyme vaccine: a cautionary tale," Epidemiol. Infect., vol. 135, pp. 1-8 (2007).
Nilsson et al., "Serum antibodies against Borrelia afzelii, Borrelia burgdorferi sensu stricto and the 41-kiloDalton flagellin in patients from a Lyme borreliosis endemic area: analysis by EIA and immunoblot," APMIS, vol. 104, No. 12, pp. 907-914 (1996).
Nowalk et al., "Serologic proteome analysis of Borrelia burgdorferi membrane-associated proteins," Infect. Immun., vol. 74, No. 7, pp. 3864-3873 (2006).
Nowalk et al., "Comparative proteome analysis of subcellular fractions from Borrelia burgdorferi by NEPHGE and IPG," Proteomics, vol. 6, pp. 2121-2134 (2006).
Ojaimi et al., "Borrelia burgdorferi gene expression profiling with membrane-based arrays," Methods Enzymol., vol. 358, pp. 165-177 (2002).
Ojaimi et al., "Comparative transcriptional profiling of Borrelia burgdorferi clinical isolates differing in capacities for hematogenous dissemination," Infect. Immun., vol. 73, No. 10, pp. 6791-6802 (2005).
Padula et al., "Molecular characterization and expression of p23 (OspC) from a North American strain of Borrelia burgdorferi," Infect. Immun., vol. 61, pp. 5097-5105 (1993).
Panelius et al., "Recombinant flagellin A proteins from Borrelia burgdorferi sensu stricto, B. afzelii, and B. Garinii in serodiagnosis of Lyme borreliosis," J. Clin. Microbiol., vol. 39, pp. 4013-4019 (2001).
Patton et al., "Functional analysis of the Borrelia burgdorferi bba64 gene product in murine infection via tick infestation," PLoS One., vol. 6, No. 5, p. e19536 (2011).
Patton et al., "Saliva, salivary gland, and hemolymph collection from Ixodes scapularis ticks," J. Vis. Exp. No. 60 (2012).
Peltomaa et al., "the V1sE 6) Peptide ELISA in the Serodiagnosis of Lyme Facial Paralysis," (1R Otol. Neurotol, vol. 25, No. 5, pp. 838-841 (2004).
Picken, R. N., "Polymerase chain reaction primers and probes derived from flagellin gene sequences for specific detection of the agents of Lyme disease and North American relapsing fever," J. Clin. Microbiol., vol. 30, No. 1, pp. 99-114 (1992).
Porcella et al., "Expression and immunological analysis of the plasmid-borne mlp genes of Borrelia burgdorferi strain B31," Infect. Immun., vol. 68, pp. 4992-5001 (2000).
Probert et al., "Identification of a 47 kDa fibronectin-binding protein expressed by Borrelia burgdorferi isolate B31," Mol. Microbiol., vol. 30, No. 5, pp. 1003-1015 (1998).
Probert et al., "Mapping the ligand-binding region of Borrelia burgdorferi fibronectin-binding protein BBK32," Infect. Immun., vol. 69, No. 6, pp. 4129-4133 (2001).
Purser et al., "Correlation between plasmid content and infectivity in Borrelia burgdorferi," Proc. Natl. Acad. Sci. USA, vol. 97, pp. 13865-13870 (2000).
Rasiah et al., "Purification and characterization of a tryptic peptide of Borrelia burgdorferi flagellin, which reduces cross-reactivity in immunoblots and ELISA," J. Gen. Microbiol., vol. 138, pp. 147-154 (1992).
Revel et al., "DNA microarray analysis of differential gene expression in Borrelia burgdorferi, the Lyme disease spirochete," Proc. Natl. Acad. Sci. USA, vol. 99, pp. 1562-1567 (2002).
Roberts et al., "Molecular analysis of sequence heterogeneity among genes encoding decorin binding proteins A and B of Borrelia burgdorferi sensu lato," Infect. Immun., vol. 66, pp. 5275-5285 (1998).
Roberts et al., "Environmental regulation and differential production of members of the Bdr protein family of Borrelia burgdorferi," Infect. Immun., vol. 70, pp. 7033-7041 (2002).
Sadziene et al., "A flagella-less mutant of Borrelia burgdorferi. Structural, molecular, and in vitro functional characterization," J. Clin. Investig., vol. 88, pp. 82-92.
Sal et al., "Borrelia burgdorferi uniquely regulates its motility genes and has an intricate flagellar hook-basal body structure," J. Bacteriol., vol. 190, No. 6, pp. 1912-1921 (2008).
Salazar et al., "Lipoprotein-Dependent and -Independent Immune Responses to Spirochetal Infection," Clin. Vaccine Immunol. vol. 12, No. 8, pp. 949-958 (2005).
Salo et al., "Decorin binding by DbpA and B of Borrelia garinii, Borrelia afzelii, and Borrelia burgdorfei sensu Stricto," J. Infect. Dis. vol. 204, No. 1, pp. 65-73 (2011).

(56) References Cited

OTHER PUBLICATIONS

Sanders et al., "Antibody levels to recombinant tick calreticulin increase in humans after exposure to Ixodes scapularis (Say) and are correlated with tick engorgement indices," Am. J. Epidemiol., vol. 149, No. 8, pp. 777-784 (1999).
Schmit et al., "Analysis of Borrelia burgdorferi Surface Proteins as Determinants in Establishing Host Cell Interactions," Front Microbiol. vol. 2, p. 141 (2011).
Schuijt et al., "Identification and characterization of Ixodes scapularis antigens that elicit tick immunity using yeast surface display," PLoS One., vol. 6, No. 1, p. e15926 (2011).
Schwalie et al., "Positive selection in tick saliva proteins of the Salp 15 family," J. Mol. Evol. vol. 68, No. 2, pp. 186-191 (2009); (Epub 2009).
Schwan et al., "Induction of an outer surface protein on Borrelia burgdorferi during tick feeding," Proc. Natl. Acad. Sci. USA, vol. 92, pp. 2909-2913 (1995).
Schwan et al., "Changes in infectivity and plasmid profile of the Lyme disease spirochete, Borrelia burgdorferi, as a result of in vitro cultivation," Infect. Immun., vol. 56, pp. 1831-1836 (1998).
Schwan et al., "Temporal changes in outer surface proteins A and C of the Lyme disease-associated spirochete, Borrelia burgdorferi, during the chain of infection in ticks and mice," J. Clin. Microbiol., vol. 38, pp. 382-388 (2000).
Schwartz et al., "Anti-tick antibodies: an epidemiologic tool in Lyme disease research," Am. J. Epidemiol., vol. 132, No. 1, pp. 58-66 (1990).
Schwartz et al., "Anti-tick saliva antibody: a biologic marker of tick exposure that is a risk factor for Lyme disease seropositivity," Am. J. Epidemiol., vol. 134, No. 1, pp. 86-95 (1991).
Schwartz et al., "Entomologic and demographic correlates of anti-tick saliva antibody in a prospective study of tick bite subjects in Westchester County, New York," Am. J. Trop. Med. Hyg. vol. 48, No. 1, pp. 50-57 (1993).
Shi et al., "Common and unique contributions of decorin-binding proteins A and B to the overall virulence of Borrelia burgdorferi," PLos One., vol. 3, No. 10, p. e3340 (2008).
Skare et al., "Cloning and molecular characterization of plasmid-encoded antigens of Borrelia burgdorferi," Infect. Immun., vol. 67, No. 9, pp. 4407-4417 (1999).
Skogman et al., "Improved laboratory diagnostics of Lyme neuroborreliosis in children by detection of antibodies to new antigens in cerebrospinal fluid," J. Pediatr. Infect. Dis., vol. 27, No. 7, pp. 605-612 (2008).
Steere et al., "Prospective study of coinfection in patients with erythema migrans," Clin. Infect. Dis., vol. 36, pp. 1078-1081 (2003).
Steere et al., "The emergence of Lyme disease," J. Clin. Investig., vol. 113, pp. 1093-1101 (2004).
Steere et al., "Therapy for Lyme arthritis: strategies for the treatment of antibiotic-refractory arthritis," Arthritis Rheum., vol. 54, pp. 3079-3086 (2006).
Stevenson et al., "A family of genes located on four separate 32-kilobase circular plasmids in Borrelia burgdorferi B31," J. Bacteriol., vol. 178, No. 12, pp. 3508-3516 (1996).
Stevenson et al., "Borrelia burgdorferi Erp proteins are immunogenic in mammals infected by tick bite, and their synthesis is inducible in cultured bacteria," Infect. Immun., vol. 66, pp. 2648-2654 (1998).
Sundaresh et al., "Identification of humoral immune responses in protein microarrays using DNA microarray data analysis techniques," Bioinformatics, vol. 22, pp. 1760-1766 (2006).
Sundaresh et al., "From protein microarrays to diagnostic antigen discovery: a study of the pathogen Francisella tularensis," Bioinformatics, vol. 23, pp. i508-18 (2007).
Tokarz et al., "Combined effects of blood and temperature shift on Borrelia burgdorferi gene expression as determined by whole-genome DNA array," Infect. Immun., vol. 72, pp. 5419-5432 (2004).
Tsao et al., "OspA immunization decreases transmission of Borrelia burgdorferi spirochetes from infected Peromyscus leucopus mice to larval Ixodes scapularis ticks," Vector Borne Zoonotic Dis., vol. 1, pp. 65-74 (2001).
Ulvestad et al., "Diagnostic and biological significance of anti-p41 IgM antibodies against Borrelia burgdorferi," Scand. J. Immunol., vol. 53, pp. 416-421 (2001).
Vaz et al., "Cellular and humoral immune responses to Borrelia burgdorferi antigens in patients with culture-positive early Lyme disease," Infect. Immun., vol. 69, No. 12, pp. 7437-7444 (2001).
Wallich et al, "The Borrelia burgdorferi flagellum-associated 41-kilodalton antigen (flagellin): molecular cloning, expression, and amplification of the gene," Infect. Immun. vol. 58, No. 6, pp. 1711-1719 (1990).
Wallich et al, "Molecular and immunological characterization of a novel polymorphic lipoprotein of Borrelia burgdorferi," Infect. Immun., vol. 61, pp. 4158-4166 (1993).
Wilske et al., "Recombinant immunoblot in the serodiagnosis of Lyme borreliosis. Comparison with indirect immunofluorescence and enzyme-linked immunosorbent assay," Med. Microbiol. Immunol., vol. 182, pp. 255-270 (1993).
Xu, et al., "A Cell Envelope Protein Array of Borrelia Burgdorferi to Profile the Humoral Response of Patients with Lyme Disease," 18th European Congress of Clinical Microbiology and Infectious Diseases (2008).
Xu, et al., "Profiling the Humoral Immune Response to Borrelia Burgdorferi Infection with Protein Microarrays," Microbial Pathogenesis, vol. 45, pp. 403-407 (2008).
Zhang et al., "bdrF2 of Lyme disease spirochetes is coexpressed with a series of cytoplasmic proteins and is produced specifically during early infection," J. Bacteriol., vol. 187, pp. 175-184 (2005).
Zΰckert et al., "Circular and linear plasmids of Lyme disease spirochetes have extensive homology: characterization of a repeated DNA element," J. Bacteriol., vol. 178, pp. 2287-2298 (1996).
Zΰckert et al., "Comparative analysis and immunological characterization of the Borrelia Bdr protein family," Infect. Immun., vol. 67, pp. 3257-3266 (1999).
International Search Report for PCT Application No. PCT;US2009/002474, dated Aug. 27, 2009.
International Preliminary Report on Patentability for PCT Application No. PCT/US2009/002474, dated Nov. 4, 2010.

* cited by examiner

| Samples | HP-NL-P1 (SEQ ID NO:1) | | HP-NL-1 (SEQ ID NO:2) | | HP-NL-2 (SEQ ID NO:3) | | HP-NL-3 (SEQ ID NO:4) | | HP-NL-P5 (SEQ ID NO:5) | | HP-[VO]2 (SEQ ID NO:6) | |
|---|---|---|---|---|---|---|---|---|---|---|---|---|
| | ECL Counts | S/B Ratio | ECL Counts | S/B Ratio | ECL Counts | S/B Ratio | ECL Counts | S/B Ratio | ECL Counts | S/B Ratio | ECL Counts | S/B Ratio |
| **Normal pooled plasma** | 165 | **1.00** | 146 | **1.00** | 202 | **1.00** | 140 | **1.00** | 925 | **1.00** | 137 | **1.00** |
| **PTL-202-1 IgG confirmed*** | 5029 | **30.5** | 14490 | **99.2** | 6216 | **30.8** | 10193 | **72.8** | 16827 | **18.2** | 21134 | **154** |
| **PTL-202-2 IgG confirmed** | 120667 | **731** | 130415 | **893** | 120990 | **599** | 156228 | **1116** | 138197 | **149** | 155083 | **1132** |
| **PTL-202-3 IgG confirmed** | 14398 | **87.3** | 23955 | **164** | 16989 | **84.1** | 15299 | **109** | 27871 | **30.1** | 33652 | **246** |
| **PTL-202-4 IgG confirmed** | 1093 | **6.6** | 1532 | **10.5** | 1535 | **7.6** | 4014 | **28.7** | 2339 | **2.5** | 3559 | **26.0** |
| **PTL-202-5 IgG confirmed** | 358 | **2.2** | 1150 | **7.9** | 716 | **3.5** | 562 | **4.0** | 2275 | **2.5** | 1409 | **10.3** |
| **PTL-202-6 IgG confirmed** | 34086 | **207** | 18373 | **126** | 25618 | **127** | 29470 | **211** | 25589 | **27.7** | 27940 | **204** |
| **PTL-202-9 Lyme-negative** | 131 | **0.8** | 131 | **0.9** | 25995 | **129** | 137 | **1.0** | 4167 | **4.5** | 16179 | **118** |

FIG. 1

| Samples | HP-NL-P1 (SEQ ID NO:1) | | HP-NL-1 (SEQ ID NO:2) | | HP-NL-2 (SEQ ID NO:3) | | HP-NL-3 (SEQ ID NO:4) | | HP-NL-P5 (SEQ ID NO:5) | | HP-[VO]2 (SEQ ID NO:6) | |
|---|---|---|---|---|---|---|---|---|---|---|---|---|
| | ECL Counts | S/B Ratio | ECL Counts | S/B Ratio | ECL Counts | S/B Ratio | ECL Counts | S/B Ratio | ECL Counts | S/B Ratio | ECL Counts | S/B Ratio |
| **Normal pooled plasma** | 283 | **1.0** | 315 | **1.0** | 469 | **1.0** | 171 | **1.0** | 170 | **1.0** | 180 | **1.0** |
| **PTL-202-1 IgM confirmed*** | 47397 | **168** | 54044 | **172** | 53654 | **114** | 6979 | **40.8** | 3508 | **20.6** | 37613 | **209** |
| **PTL-202-2 IgG confirmed** | 191 | **0.7** | 181 | **0.6** | 204 | **0.4** | 141 | **0.8** | 135 | **0.8** | 171 | **1.0** |
| **PTL-202-3 IgG confirmed** | 556 | **1.9** | 487 | **1.5** | 773 | **1.6** | 715 | **4.2** | 297 | **1.7** | 649 | **3.6** |
| **PTL-202-4 IgG confirmed** | 245 | **0.9** | 227 | **0.7** | 280 | **0.6** | 225 | **1.3** | 158 | **0.9** | 198 | **1.1** |
| **PTL-202-5 IgM confirmed** | 5960 | **21.1** | 69468 | **221** | 11125 | **23.7** | 27575 | **161** | 62422 | **367** | 59682 | **332** |
| **PTL-202-6 IgG confirmed** | 135 | **0.5** | 137 | **0.4** | 133 | **0.3** | 129 | **0.8** | 123 | **0.7** | 132 | **0.7** |
| **PTL-202-9 Lyme-negative** | 141 | **0.5** | 152 | **0.5** | 182 | **0.4** | 144 | **0.8** | 137 | **0.8** | 164 | **0.9** |

FIG. 2

| Plasma Sample | BBA25/ BB0147/ HP-NL-P1 | BBA64/ BB0147/ HP-NL-P1 | BBA64/ BB0147/ HP-NL-3 | BBA64/ BB0283 | HP-NL-3/ HP-NL-P5 | BBA64/ BB0147 | BBA64/ BB0283/ BBA25 | BBA64/ BB0283/ BB0147 |
|---|---|---|---|---|---|---|---|---|
| | Mixture 1 S/B ratio | Mixture 2 S/B ratio | Mixture 3 S/B ratio | Mixture 4 S/B ratio | Mixture 5 S/B ratio | Mixture 6 S/B ratio | Mixture 7 S/B ratio | Mixture 8 S/B ratio |
| Normal pooled plasma | 1.0 | 1.0 | 1.0 | 1.0 | 1.0 | 1.0 | 1.0 | 1.0 |
| High positive (positive control) | 318 | 94.4 | 115 | 10.7 | 233 | 18.7 | 159 | 14.3 |
| Lyme-positive 1 (IgG and IgM) | 80 | 26.2 | 57.3 | 1.9* | 285 | 8.0 | 37 | 7.1 |
| Lyme-positive 2 (IgG only) | 22.1 | 14 | 31.1 | 1.6* | 77.9 | 1.7* | 3.9 | 1.5* |
| Lyme-positive 3 (IgG and IgM) | 77.6 | 16 | 20 | 2.5 | 30.2 | 4.0 | 36.7 | 3.3 |
| Lyme-negative (normal donor) | 0.9 | 2.4/eq | 2.4/eq | 3.7* | 0.9 | 3.4* | 2.2/eq | 2.4/eq |

FIG. 3

| Plasma Sample | BBA25/ BB0147/ HP-NL-P1 | BBA64/ BB0147/ HP-NL-P1 | BBA64/ BB0147/ HP-NL-3 | BBA64/ BB0283 | HP-NL-3/ HP-NL-P5 | BBA64/ BB0147 | BBA64/ BB0283/ BBA25 | BBA64/ BB0283/ BB0147 |
|---|---|---|---|---|---|---|---|---|
| | Mixture 1 S/B ratio | Mixture 2 S/B ratio | Mixture 3 S/B ratio | Mixture 4 S/B ratio | Mixture 5 S/B ratio | Mixture 6 S/B ratio | Mixture 7 S/B ratio | Mixture 8 S/B ratio |
| Normal pooled plasma | 1.0 | 1.0 | 1.0 | 1.0 | 1.0 | 1.0 | 1.0 | 1.0 |
| High positive (positive control) | 180 | 176 | 39.4 | 9.4 | 52.5 | 20.2 | 75.1 | 11.5 |
| Lyme-positive 1 (IgG and IgM) | 6.4 | 6.7 | 2.3/eq | 2.5 | 2.7 | 2.6 | 4.2 | 3.9 |
| Lyme-positive 2 (IgG only) | 1.3 | 1.2 | 1.3 | 1.0 | 1.4 | 1.0 | 1.0 | 1.0 |
| Lyme-positive 3 (IgG and IgM) | 2.7 | 2.5 | 1.3* | 1.0* | 1.3* | 1.1* | 1.5* | 1.0* |
| Lyme-negative (normal donor) | 1.0 | 1.0 | 1.0 | 1.0 | 1.0 | 1.1 | 1.0 | 1.0 |

FIG. 4

| Plasma Sample | IgG Detection | | | | | |
|---|---|---|---|---|---|---|
| | Day 1 | | Day 2 | | Day 3 | |
| | ECL Count | S/B Ratio | ECL Count | S/B Ratio | ECL Count | S/B Ratio |
| Negative Control | 184 | **1.0** | 193 | **1.0** | 198 | **1.0** |
| Positive Control | 52623 | **286** | 59340 | **308** | 59151 | **299** |
| PSG 11650 Confirmed IgG/IgM Positive | 16392 | **89.1** | 17994 | **93.2** | 19158 | **96.8** |
| LS1147377 Confirmed IgG Positive IgM Negative | 4370 | **23.7** | 4798 | **24.9** | 4632 | **23.4** |
| LS1147304 Confirmed IgG Positive Low IgM Positive | 16339 | **88.8** | 15776 | **81.7** | 15598 | **78.8** |
| BRH805538 Healthy Donor (Lyme Negative) | 169 | **0.9** | 174 | **0.9** | 185 | **0.9** |
| BRH460640 Low IgG Positive | 2461 | **13.4** | 2642 | **13.7** | 2569 | **13** |
| BRH460641 Low IgG Positive | 1438 | **7.8** | 1653 | **8.6** | 1344 | **6.8** |

FIG. 5

| Plasma Sample | **IgM Detection** | | | | | |
|---|---|---|---|---|---|---|
| | Day 1 | | Day 2 | | Day 3 | |
| | ECL Count | S/B Ratio | ECL Count | S/B Ratio | ECL Count | S/B Ratio |
| Negative Control | 142 | **1.0** | 142 | **1.0** | 145 | **1.0** |
| Positive Control | 23012 | **162** | 26762 | **189** | 26028 | **180** |
| PSG 11650<br>Confirmed IgG/IgM Positive | 1379 | **9.7** | 1288 | **9.1** | 1461 | **10.1** |
| LS1147377<br>Confirmed IgG Positive<br>IgM Negative | 177 | **1.2** | 183 | **1.3** | 179 | **1.2** |
| LS1147304<br>Confirmed IgG Positive<br>Low IgM Positive | 563 | **4.0** | 441 | **3.1** | 359 | **2.5** |
| BRH805538<br>Healthy Donor<br>(Lyme Negative) | 138 | **1.0** | 141 | **1.0** | 139 | **1.0** |
| BRH460640<br>Low IgG Positive | 186 | **1.3** | 197 | **1.4** | 183 | **1.3** |
| BRH460641<br>Low IgG Positive | 146 | **1.0** | 153 | **1.1** | 145 | **1.0** |

FIG. 6

| Sample | ECL Lyme Assay | | | |
|---|---|---|---|---|
| | IgM Detector | | IgG Detector | |
| | ECL Count | S/B Ratio | ECL Count | S/B Ratio |
| Negative control | 143 | 1.0 | 299 | 1.0 |
| Positive control | 78027 | 546 | 155192 | 519 |
| PS40 | 146 | 1.0 | 240 | 1.0 |
| PS41 | 155 | 1.1 | 270 | 1.0 |
| PS42 | 3912 | 27.5 | 3829 | 12.8 |
| PS43 | 938 | 6.6 | 4030 | 13.5 |
| PS44 | 695 | 4.9 | 33692 | 113 |
| PS45 | 878 | 6.2 | 6209 | 20.8 |
| PS46 | 158 | 1.1 | 224 | 0.9 |
| PS47 | 229 | 1.6 | 288 | 1.0 |
| PS48 | 1491 | 10.5 | 36629 | 123 |
| PS49 | 1608 | 11.3 | 118575 | 397 |
| PS50 | 209 | 1.5 | 104443 | 349 |
| PS51 | 622 | 4.4 | 112277 | 376 |
| PS52 | 147 | 1.0 | 275 | 1.1 |
| PS53 | 142 | 1.0 | 246 | 1.0 |
| PS54 | 185 | 1.2 | 467 | 1.9 |
| PS55 | 165 | 1.1 | 239 | 0.9 |
| PS56 | 236 | 1.6 | 217 | 0.9 |
| PS57 | 181 | 1.2 | 241 | 0.9 |
| PS58 | 564 | 4.0 | 703 | 2.4 |
| PS59 | 164 | 1.1 | 247 | 1.0 |
| PS60 | 146 | 1.0 | 195 | 0.8 |
| PS61 | 150 | 1.0 | 241 | 0.9 |
| PS62 | 147 | 1.0 | 259 | 1.0 |
| PS63 | 179 | 1.3 | 389 | 1.3 |
| PS64 | 252 | 1.8 | 222 | 0.7 |
| PS65 | 176 | 1.2 | 673 | 2.2 |
| PS66 | 143 | 1.0 | 219 | 0.8 |
| PS67 | 191 | 1.3 | 329 | 1.3 |
| PS68 | 272 | 1.8 | 313 | 1.2 |
| PS69 | 161 | 1.1 | 400 | 1.6 |
| PS70 | 146 | 1.0 | 260 | 1.1 |
| PS71 | 186 | 1.3 | 332 | 1.3 |

FIG. 7

| # | Confirmed Clinical Diagnosis | *ECL Lyme Assay (S/B ratio)(pos>2.5)* | | | CDC 2-Tier Testing | | | |
|---|---|---|---|---|---|---|---|---|
| | | IgM | IgG | RESULT | 1st tier EIA | 2nd tier WB- IgM | 2nd tier WB-IgG | RESULT |
| PS40 | Lyme 1 (Early-EM) | 1.0 | 1.0 | NEG | Neg | Neg | Neg | NEG |
| PS41 | Lyme 1 (Early-EM) | 1.1 | 1.0 | NEG | Neg | Neg | Neg | NEG |
| PS42 | Lyme 1 (Early-EM) | 27.5 | 12.8 | POS | Pos | Pos | Neg | POS |
| PS43 | Lyme 1 (Early-EM) | 6.6 | 13.5 | POS | Pos | Pos | Neg | POS |
| PS44 | Lyme 1 (Early-EM) | 4.9 | 112.7 | POS | Pos | Pos | Pos | POS |
| PS45 | Lyme 1 (Early-EM) | 6.2 | 20.8 | POS | Pos | Pos | Neg | POS |
| PS46 | Lyme 1 (Early-EM) | 1.1 | 0.9 | NEG | Neg | Neg | Neg | NEG |
| PS47 | Lyme 1 (Early-EM) | 1.6 | 1.0 | NEG | Neg | Pos | Neg | NEG |
| PS48 | Lyme 2 (Neurologic) | 10.5 | 122.5 | POS | Pos | Pos | Pos | POS |
| PS49 | Lyme 2 (Neurologic) | 11.3 | 396.6 | POS | Pos | Pos | Pos | POS |
| PS50 | Lyme 3 (Arthritis) | 1.5 | 349.3 | POS | Pos | Neg | Pos | POS |
| PS51 | Lyme 3 (Arthritis) | 4.4 | 375.5 | POS | Pos | Pos | Pos | POS |
| PS52 | Rheumatoid Arthritis | 1.0 | 1.1 | NEG | Neg | Neg | Neg | NEG |
| PS53 | Rheumatoid Arthritis | 1.0 | 1.0 | NEG | Neg | Neg | Neg | NEG |
| PS54 | Syphilis | 1.2 | 1.9 | NEG | Pos | Neg | Neg | NEG |
| PS55 | Syphilis | 1.1 | 0.9 | NEG | Neg | Neg | Neg | NEG |
| PS56 | Fibromyalgia | 1.6 | 0.9 | NEG | Neg | Neg | Neg | NEG |
| PS57 | Fibromyalgia | 1.2 | 0.9 | NEG | Neg | Neg | Neg | NEG |
| PS58 | Mononucleosis | 4.0 | 2.4 | POS | Pos | Neg | Neg | NEG |
| PS59 | Mononucleosis | 1.1 | 1.0 | NEG | Neg | Neg | Neg | NEG |
| PS60 | Severe periodontitis | 1.0 | 0.8 | NEG | Neg | Neg | Neg | NEG |
| PS61 | Severe periodontitis | 1.0 | 0.9 | NEG | Neg | Neg | Neg | NEG |
| PS62 | Multiple Sclerosis | 1.0 | 1.0 | NEG | Neg | Neg | Neg | NEG |
| PS63 | Multiple Sclerosis | 1.3 | 1.3 | NEG | Neg | Neg | Neg | NEG |
| PS64 | Healthy non-endemic | 1.8 | 0.7 | NEG | Pos | Neg | Neg | NEG |
| PS65 | Healthy non-endemic | 1.2 | 2.2 | NEG | Neg | Neg | Neg | NEG |
| PS66 | Healthy non-endemic | 1.0 | 0.8 | NEG | Neg | Neg | Neg | NEG |
| PS67 | Healthy non-endemic | 1.3 | 1.3 | NEG | Neg | Neg | Neg | NEG |
| PS68 | Healthy endemic | 1.8 | 1.2 | NEG | Pos | Neg | Neg | NEG |
| PS69 | Healthy endemic | 1.1 | 1.6 | NEG | Neg | Neg | Neg | NEG |
| PS70 | Healthy endemic | 1.0 | 1.1 | NEG | Neg | Neg | Neg | NEG |
| PS71 | Healthy endemic | 1.3 | 1.3 | NEG | Neg | Neg | Neg | NEG |

FIG. 8

| Samples | Clinical Diagnosis | *ECL Lyme Assay (pos≥15)* | | | *CDC Two-Tier Data* | |
|---|---|---|---|---|---|---|
| | | *IgG S/B Ratio* | *IgM S/B Ratio* | *Result* | *1st Tier Result* | *Two-Tier Result* |
| PS72 | Lyme Early-EM | **251** | **381** | **POS** | **POS** | **POS** |
| PS73 | Lyme Early-EM | **360** | **24** | **POS** | **POS** | **POS** |
| PS74 | Lyme Early-EM | **1.0** | **1.0** | NEG | NEG | NEG |
| PS75 | Lyme Early-EM | **81** | **9.0** | ***POS*** | ***POS*** | *NEG* |
| PS76 | Lyme Early-EM | **1.0** | **6.0** | NEG | ***POS*** | NEG |
| PS77 | Lyme Early-EM | **1.0** | **2.0** | NEG | NEG | NEG |
| PS78 | Lyme Early-EM | **282** | **10** | **POS** | **POS** | **POS** |
| PS79 | Lyme Early-EM | **1.0** | **1.0** | NEG | NEG | NEG |
| PS80 | Lyme Early-EM | **64** | **10** | ***POS*** | ***POS*** | *NEG* |
| PS81 | Lyme Early-EM | **574** | **13** | **POS** | **POS** | **POS** |
| PS82 | Lyme Early-EM | **158** | **21** | **POS** | **POS** | **POS** |
| PS83 | Lyme Early-EM | **18** | **7** | **POS** | **POS** | **POS** |
| PS84 | Lyme Early-EM | **1.0** | **5.0** | NEG | EQ | NEG |
| PS85 | Lyme Early-EM | **74** | **10** | ***POS*** | ***POS*** | *NEG* |
| PS86 | Lyme Early-EM | **1.0** | **1.0** | NEG | NEG | NEG |
| PS87 | Lyme Early-EM | **37** | **27** | **POS** | **POS** | **POS** |
| PS88 | Lyme Early-EM | **1.0** | **1.0** | NEG | EQ | NEG |
| PS89 | Lyme Early-EM | **194** | **8.0** | ***POS*** | ***POS*** | *NEG* |
| PS90 | Lyme Early-EM | **2.0** | **4.0** | NEG | NEG | NEG |
| PS91 | Lyme Early-EM | **302** | **46** | **POS** | **POS** | **POS** |

FIG. 9

| Samples | Clinical Diagnosis | *ECL Lyme Assay (pos ≥15)* | | | *CDC Two-Tier Result* | |
|---|---|---|---|---|---|---|
| | | *IgG S/B Ratio* | *IgM S/B Ratio* | *Result* | *1st Tier Result* | *Two-Tier Result* |
| PS92 | Lyme Early Cardiac | **541** | **885** | **POS** | **POS** | **POS** |
| PS93 | Lyme Early Cardiac | **715** | **21** | **POS** | **POS** | **POS** |
| PS94 | Lyme Early Neurologic | **19** | **27** | ***POS*** | *NEG* | *NEG* |
| PS95 | Lyme Early Neurologic | **248** | **43** | **POS** | **POS** | **POS** |
| PS96 | Lyme Early Neurologic | **63** | **24** | **POS** | **POS** | **POS** |
| PS97 | Lyme Early Neurologic | **346** | **23** | **POS** | **POS** | **POS** |
| PS98 | Lyme Late Arthritis | **1187** | **6.0** | **POS** | **POS** | **POS** |
| PS99 | Lyme Late Arthritis | **226** | **5.0** | **POS** | **POS** | **POS** |
| PS100 | Lyme Late Arthritis | **1437** | **6.0** | **POS** | **POS** | **POS** |
| PS101 | Lyme Late Arthritis | **625** | **5.0** | **POS** | **POS** | **POS** |
| PS102 | Lyme Late Arthritis | **416** | **10** | **POS** | **POS** | **POS** |
| PS103 | Lyme Late Arthritis | **385** | **20** | **POS** | **POS** | **POS** |

FIG. 10

| Samples | Clinical Diagnosis | ECL Lyme Assay (pos≥15) | | | CDC Two-Tier Data | |
|---|---|---|---|---|---|---|
| | | IgG S/B Ratio | IgM S/B Ratio | Result | 1st Tier Result | Two-Tier Result |
| PS104 | Healthy non-endemic | 1.0 | 2.0 | NEG | NEG | NEG |
| PS105 | Healthy non-endemic | 4.0 | 5.0 | NEG | NEG | NEG |
| PS106 | Healthy non-endemic | 1.0 | 1.0 | NEG | NEG | NEG |
| PS107 | Healthy non-endemic | 1.0 | 1.0 | NEG | POS | NEG |
| PS108 | Healthy non-endemic | 1.0 | 4.0 | NEG | NEG | NEG |
| PS109 | Healthy non-endemic | 1.0 | 1.0 | NEG | NEG | NEG |
| PS110 | Healthy non-endemic | 1.0 | 1.0 | NEG | NEG | NEG |
| PS111 | Healthy non-endemic | 1.0 | 1.0 | NEG | NEG | NEG |
| PS112 | Healthy non-endemic | 1.0 | 1.0 | NEG | EQ | NEG |
| PS113 | Healthy non-endemic | 1.0 | 1.0 | NEG | NEG | NEG |
| PS114 | Healthy non-endemic | 1.0 | 1.0 | NEG | NEG | NEG |
| PS115 | Healthy non-endemic | 1.0 | 1.0 | NEG | NEG | NEG |
| PS116 | Healthy endemic | 1.0 | 1.0 | NEG | NEG | NEG |
| PS117 | Healthy endemic | 1.0 | 1.0 | NEG | NEG | NEG |
| PS118 | Healthy endemic | 1.0 | 3.0 | NEG | NEG | NEG |
| PS119 | Healthy endemic | 1.0 | 1.0 | NEG | NEG | NEG |
| PS120 | Healthy endemic | 1.0 | 4.0 | NEG | NEG | NEG |
| PS121 | Healthy endemic | 1.0 | 2.0 | NEG | NEG | NEG |
| PS122 | Healthy endemic | 13 | 2.0 | NEG | POS | NEG |
| PS123 | Healthy endemic | 1.0 | 1.0 | NEG | POS | NEG |
| PS124 | Healthy endemic | 1.0 | 13 | NEG | EQ | NEG |
| PS125 | Healthy endemic | 1.0 | 1.0 | NEG | POS | NEG |
| PS126 | Healthy endemic | 1.0 | 1.0 | NEG | NEG | NEG |
| PS127 | Healthy endemic | 1.0 | 1.0 | NEG | NEG | NEG |

FIG. 11

| Samples | Clinical Diagnosis | ECL Lyme Assay (pos ≥ 15) | | | CDC Two-Tier Results | |
|---|---|---|---|---|---|---|
| | | IgG S/B Ratio | IgM S/B Ratio | Result | 1st Tier Result | Two-Tier Result |
| PS128 | Severe periodontitis | 1.0 | 1.0 | NEG | NEG | NEG |
| PS129 | Severe periodontitis | 1.0 | 2.0 | NEG | NEG | NEG |
| PS130 | Severe periodontitis | 1.0 | 1.0 | NEG | NEG | NEG |
| PS131 | Severe periodontitis | 1.0 | 1.0 | NEG | NEG | NEG |
| PS132 | Severe periodontitis | 1.0 | 1.0 | NEG | NEG | NEG |
| PS133 | Severe periodontitis | 1.0 | 1.0 | NEG | NEG | NEG |
| PS134 | Fibromyalgia | 1.0 | 1.0 | NEG | NEG | NEG |
| PS135 | Fibromyalgia | 1.0 | 3.0 | NEG | NEG | NEG |
| PS136 | Fibromyalgia | 67 | 2.0 | POS | NEG | NEG |
| PS137 | Fibromyalgia | 1.0 | 1.0 | NEG | NEG | NEG |
| PS138 | Fibromyalgia | 4.0 | 1.0 | NEG | NEG | NEG |
| PS139 | Fibromyalgia | 106 | 7.0 | POS | NEG | NEG |
| PS140 | Mononucleosis | 2.0 | 1.0 | NEG | NEG | NEG |
| PS141 | Mononucleosis | 1.0 | 1.0 | NEG | POS | NEG |
| PS142 | Mononucleosis | 1.0 | 1.0 | NEG | NEG | NEG |
| PS143 | Mononucleosis | 1.0 | 1.0 | NEG | NEG | NEG |
| PS144 | Mononucleosis | 2.0 | 9.0 | NEG | POS | NEG |
| PS145 | Mononucleosis | 1.0 | 1.0 | NEG | EQ | NEG |
| PS146 | Rheumatoid arthritis | 4.0 | 1.0 | NEG | NEG | NEG |
| PS147 | Rheumatoid arthritis | 3.0 | 1.0 | NEG | NEG | NEG |
| PS148 | Rheumatoid arthritis | 1.0 | 1.0 | NEG | NEG | NEG |
| PS149 | Rheumatoid arthritis | 1.0 | 1.0 | NEG | NEG | NEG |
| PS150 | Rheumatoid arthritis | 1.0 | 3.0 | NEG | POS | NEG |
| PS151 | Rheumatoid arthritis | 1.0 | 63 | POS | POS | POS |
| PS152 | Syphilis | 2.0 | 1.0 | NEG | NEG | NEG |
| PS153 | Syphilis | 1.0 | 1.0 | NEG | POS | NEG |
| PS154 | Syphilis | 1.0 | 4.0 | NEG | POS | POS |
| PS155 | Syphilis | 1.0 | 1.0 | NEG | POS | NEG |
| PS156 | Syphilis | 1.0 | 2.0 | NEG | POS | NEG |
| PS157 | Syphilis | 1.0 | 2.0 | NEG | POS | NEG |
| PS158 | Multiple sclerosis | 1.0 | 1.0 | NEG | NEG | NEG |
| PS159 | Multiple sclerosis | 6.0 | 2.0 | NEG | NEG | NEG |
| PS160 | Multiple sclerosis | 1.0 | 1.0 | NEG | NEG | NEG |
| PS161 | Multiple sclerosis | 0.0 | 3.0 | NEG | NEG | NEG |
| PS162 | Multiple sclerosis | 1.0 | 1.0 | NEG | NEG | NEG |
| PS163 | Multiple sclerosis | 9.0 | 1.0 | NEG | POS | NEG |

FIG. 12

| *Confirmed Clinical Diagnosis* | *# Samples* | *ECL Lyme Assay Result* | *CDC Data: First Tier Result* | *CDC Data: Two-Tier Result* |
|---|---|---|---|---|
| Early Lyme/EM (convalescent) | 17 | 16 (+), 1 (-) | 17 (+) | 12 (+), 5 (-) |
| Early Lyme/EM (no detectable Abs) | 11 | 11 (-) | 11 (-) | 11 (-) |
| Early Lyme Neurologic/Cardiac | 8 | 8 (+) | 7 (+), 1 false (-) | 7 (+), 1 false (-) |
| Late Lyme Arthritis | 8 | 8 (+) | 8 (+) | 8 (+) |
| Control Healthy Endemic | 16 | 16 (-) | 12 (-), 4 false (+) | 16 (-) |
| Control Healthy Non-endemic | 16 | 16 (-) | 14 (-), 2 false (+) | 16 (-) |
| Control Multiple Sclerosis | 8 | 8 (-) | 7 (-), 1 false (+) | 8 (-) |
| Control Fibromyalgia | 8 | 6 (-), 2 false (+) | 8 (-) | 8 (-) |
| Control Syphilis | 8 | 8 (-) | 2 (-), 6 false (+) | 7 (-),1 false (+) |
| Control Severe Periodontitis | 8 | 8 (-) | 8 (-) | 8 (-) |
| Control Mononucleosis | 8 | 7 (-), 1 false (+) | 5 (-), 3 false (+) | 8 (-) |
| Control Rheumatoid Arthritis | 8 | 7 (-), 1 false (+) | 6 (-), 2 false (+) | 7 (-),1 false (+) |

FIG. 13

COMPOSITIONS AND METHODS FOR THE DIAGNOSIS OF LYME DISEASE

FIELD

This is a national stage application of International Application No. PCT/US2015/051665, filed internationally on Sep. 23, 2015, which claims priority to U.S. Provisional Patent Application No. 62/054,671, filed Sep. 24, 2014, each of which is herein incorporated by reference in its entirety.

The present disclosure relates to the detection and diagnosis of Lyme disease. In particular, the present disclosure relates to antigen compositions and methods used to detect anti-*Borrelia* antibodies in a sample to aid in the diagnosis of Lyme disease.

BACKGROUND

Lyme disease is the most common vector-borne disease in the United States. The disease is caused by the spirochetal pathogen *Borrelia burgdorferi* (or other *Borrelia* species) transmitted by ticks of the genus *Ixodes*. Human infection can result in musculoskeletal, neurologic or cardiovascular disorders, which are normally present in three phases: (1) early localized disease; (2) early disseminated disease; and (3) late Lyme disease. The clinical features of each phase can overlap, and some patients present in later phases of the disease without previously having symptoms of earlier phases of the disease. Early localized disease starts with a characteristic skin rash called erythema migrans (EM). The EM rash is followed by Spirochetemia caused by early wide-spread dissemination of the bacteria through tissue and body fluids, and later chronic major manifestations if the patient remains untreated.

Clinical diagnosis of Lyme disease is usually based on a typical EM rash in the early stage of the disease, and treatment of the disease with oral antibiotics is generally effective at the early stage. However, the EM rash can be either missed (e.g., it usually disappears in a few days) or not present in an infected person (e.g., occurs in 70-80% of infected people). Without a confirmed EM rash, a clear diagnosis of Lyme disease can be difficult for a number of reasons, one of which is lack of specific signs and symptoms. For example, Lyme disease may mimic other conditions, such as chronic fatigue, multiple sclerosis, rheumatoid arthritis, and other diseases with multiple symptoms involving different body systems.

Laboratory testing methods have become the supportive tool for early diagnosis of the disease for patients without specific symptoms. The most common laboratory-based diagnostic approach is serological testing to detect antibodies to *Borrelia* species in the blood. Due to the high rate of false-positive and false-negative results of existing serological tests, the Center for Disease Control and Prevention, National Center for Emerging and Zoonotic Infectious Diseases (CDC) recommends a two-tiered testing approach. The two-tiered test includes the following steps: (1) a conventional enzyme-linked immunoassay (ELISA) test, followed by (2) a Western Blot (WB) test if the initial ELISA test is positive or equivocal. However, because of the potential for misleading results (e.g., a false-positive due to lack of *Borrelia* antigen specificity or a false-negative due to insufficient *Borrelia* antigen presentation in the subject), current laboratory tests often cannot establish the diagnosis, even when using the CDC-recommended two-tier testing. Thus, the two-tiered approach has limitations causing delay in the treatment of Lyme disease and potentially resulting in the subject developing serious complications and chronic symptoms.

The challenges surrounding the diagnosis of Lyme disease call for the improvement of current diagnostic tests, particularly in terms of sensitivity and specificity. Generally, the testing of a subject's blood for evidence of Lyme disease requires measurements of a subject's specific antibodies, such as IgM and/or IgG, in response to exposure to the *Borrelia* antigens. Commercially available diagnostic assays for Lyme disease are often insensitive, may result in false-positive or false-negative results, may have high costs, and subjective interpretation of results. The necessity to improve accuracy of Lyme diagnostics calls for implementation of tests which incorporates a unique selection of highly-immunogenic antigens to add specificity and sensitivity of the detection of antibodies to *Borrelia*, the causative agent of Lyme disease, in human blood.

SUMMARY

There are disclosed antigenic compositions that comprise a mixture of *Borrelia* antigens, and methods and kits useful for the diagnosis of various diseases, including Lyme disease.

The disclosure relates generally to methods for detecting antibodies to a disease-causing agent in a sample from a subject suspected of having the disease, the methods comprising contacting the sample with at least three capture moieties and a detection moiety and detecting a signal from the detection moiety, wherein each of the at least three capture moieties is capable of forming at least one complex with at least one antibody to the disease-causing agent in the sample, wherein the detection moiety binds to the antibody of the antibody-capture moiety complex, wherein the formation of the at least one complex is indicative of the presence of an antibody to the disease-causing agent in the sample, and wherein the amount of signal detected is directly proportional to the anti-disease-causing agent antibody in the sample.

The disclosure relates generally to methods for detecting antibodies to Lyme disease in a sample from a subject suspected of having Lyme disease, the methods comprising contacting the sample with three capture moieties and a detection moiety; and detecting a signal from the detection moiety, wherein the three capture moieties are selected from the group consisting of a BBA25 (Decorin binding protein B) protein, a BB0147 (Flagellar filament (FlaB)) protein, and a hybrid peptide comprising an amino acid sequence of SEQ ID NO:1, and each is capable of forming at least one complex with at least one antibody to a *Borrelia* antigen in the sample, wherein the detection moiety binds to the antibody of the antibody-capture moiety complex, wherein the formation of the at least one complex is indicative of the presence of an anti-*Borrelia* antibody to the *Borrelia* antigen in the sample, and wherein the amount of signal detected is directly proportional to the anti-*Borrelia* antibody in the sample.

The disclosure generally relates to kits for detecting an anti-*Borrelia* antibody in a sample or for diagnosing Lyme disease, comprising the compositions disclosed herein, wherein the antigens of the mixture are capable of binding to an antibody of a subject with Lyme disease (or suspected of having Lyme disease) to form an antibody-antigen complex; and a labeled component capable of binding to the antibody of the antibody-antigen complex for detection.

Apart from the subject matter discussed above, the present disclosure includes a number of other exemplary features such as those explained hereinafter. It is to be understood that both the foregoing and the following descriptions are exemplary only.

BRIEF DESCRIPTION OF THE DRAWINGS

FIG. 1 is a table providing the results for ECL Lyme assay performance of hybrid peptides with IgG detector.

FIG. 2 is a table providing the results for ECL Lyme assay performance of hybrid peptides with IgM detector.

FIG. 3 is a table providing the results for ECL Lyme assay with combinations of Lyme antigens and IgG detector.

FIG. 4 is a table providing the results for ECL Lyme assay with combinations of Lyme antigens and IgM detector.

FIG. 5 is a table providing the results for reproducibility of ECL Lyme assay with IgG detector.

FIG. 6 is a table providing the results for reproducibility of ECL Lyme assay with IgM detector.

FIG. 7 is a table providing the results for data from ECL Lyme assay with IgG and IgM detectors.

FIG. 8 is a table providing a comparison of results from the ECL Lyme assay and the CDC two-tier testing.

FIG. 9 is a table providing a comparison of results from the ECL Lyme assay to the CDC Research Lyme Panel II: samples of patients with early Lyme disease and erythema migrans (EM).

FIG. 10 is a table providing a comparison of results from the ECL Lyme assay to the CDC Research Lyme Panel II: samples of patients with non-EM and late Lyme disease.

FIG. 11 is a table providing a comparison of results from the ECL Lyme assay to the CDC Research Lyme Panel II: samples of normal donors from Lyme endemic and non-endemic areas.

FIG. 12 is a table providing a comparison of results from the ECL Lyme assay to the CDC Research Lyme Panel II: samples of patients with potentially cross-reactive diseases.

FIG. 13 is a table providing a summary of testing of CDC research Lyme panels I and II (human samples).

BRIEF DESCRIPTION OF THE SEQUENCES

SEQ ID NO:1 is the amino acid sequence of a hybrid peptide containing amino acid sequences from *Borrelia* antigens.

SEQ ID NO:2 is the amino acid sequence of a hybrid peptide containing amino acid sequences from *Borrelia* antigens.

SEQ ID NO:3 is the amino acid sequence of a hybrid peptide containing amino acid sequences from *Borrelia* antigens.

SEQ ID NO:4 is the amino acid sequence of a hybrid peptide containing amino acid sequences from *Borrelia* antigens.

SEQ ID NO:5 is the amino acid sequence of a hybrid peptide containing amino acid sequences from *Borrelia* antigens.

SEQ ID NO:6 is the amino acid sequence of a hybrid peptide containing amino acid sequences from *Borrelia* antigens.

SEQ ID NO:7 is the amino acid sequence of a recombinant *Borrelia* protein, BBA25 (dbpB decorin binding protein B).

SEQ ID NO:8 is the amino acid sequence of a recombinant *Borrelia* protein, BB0147 (flaB flagellar filament 41 kDa core protein).

DETAILED DESCRIPTION

Definitions. Unless specifically defined otherwise herein, all technical, scientific, and other terms used herein have the same meaning as commonly understood by one of ordinary skill in the art of immunoassays and related sciences.

The term "antigen" as used herein, refers to a protein or polypeptide capable of generating an immune response in the form of an antibody. An antigen may comprise one or more epitopes that bind specific antibodies.

The term "antigen composition" as used herein, refers to a combination of antigenic proteins, peptides, hybrid peptides, or other antigenic components that can be used as part of the capture moiety.

The term "assay component" as used herein, refers to the individual components that may be used in performing an assay. Non-limiting examples of assay components include reagents, buffers, antibodies, antigens, solid support, labels.

The term "binding partner" as used herein, refers to an organic molecule that is capable of binding an immunoglobulin. Non-limiting examples of binding partners include antibodies, antigens, protein A, protein G, aptamers, or nucleic acids, for detection in an assay.

The term "*Borrelia* species" as used herein, refers to any *Borrelia* species known to cause Lyme disease or Lyme-like illness. Non-limiting examples include *Borrelia afzelii, Borrelia burgdorferi, Borrelia garinii, Borrelia miyamotoi*, and *Borrelia valaisiana.*

The terms "capture moiety," "capture reagent," and "capture bead" as used herein, refer to an antigen or an antigen composition attached to a solid support.

The term "detection moiety" as used herein, refers to a binding partner attached to a label that is detectable and/or capable of producing a detectable signal. The label can be attached, directly or indirectly, to various binding partners. An example of a detection moiety is a detector antibody that may be an anti-human antibody that is capable of binding to the antibody portion of the antibody-antigen complex formed in the methods disclosed herein. Commercially available anti-human antibodies may be suitable for use with the methods herein. Other detection antibodies for others species may be used.

The term "epitope" as used herein, refers to a portion of an antigen that is specifically recognized by an antibody.

The term "hybrid peptide" as used herein, refers to a combination of or the combining of synthetic amino acid sequences containing, in part, amino acid sequences from two or more naturally occurring polypeptides combined into one sequence. The hybrid peptides may be produced using known recombinant techniques or chemical synthesis.

The term "sample" as used herein, refers to a biological material that is known to or suspected of containing an analyte, such as an antibody or antigen. Non-limiting examples of samples include blood, plasma, serum, urine, saliva, or tissue cells.

The term "solid support" as used herein, refers to any material that is insoluble and/or has structural rigidity and resistance to changes of shape or volume, and to which an antigen can be immobilized or bound.

The term "subject" as used herein, refers to any organism which is susceptible to a *Borrelia* species infection. Non-limiting examples of subjects include humans, dogs, cats and horses.

Additional terms may be defined, as required, in the disclosure that follows.

In one aspect of the present disclosure, methods for detecting antibodies to a disease-causing agent in a sample from a subject suspected of having the disease are disclosed, the methods comprising contacting the sample with at least three capture moieties and a detection moiety and detecting a signal from the detection moiety. Each of the at least three capture moieties is capable of forming at least one complex with at least one antibody to the disease-causing agent in the sample. The detection moiety binds to the antibody of the antibody-capture moiety complex. The formation of the at least one complex is indicative of the presence of an antibody to the disease-causing agent in the sample. The amount of signal detected is directly proportional to the anti-disease-causing agent antibody in the sample.

The use of at least three capture moieties is capable of increasing the sensitivity of the methods disclosed herein due to their ability to bind to more antigens seeking a variety of antibodies in the sample. The increase in these interactions increases the signal produced in an assay above any background.

In some embodiments, each of the at least three capture moieties may include a solid support and an antigen of the disease-causing agent in the sample. For any of the diseases being detected, the antigens being used in the assay methods would correlate to the disease-causing agent. In some embodiments, the antigen may be a peptide, a protein, a recombinant protein, a polypeptide or a hybrid peptide.

The methods disclosed herein, can be used for many diseases, for example, Lyme disease. In some embodiments, the disease being detected is Lyme disease. For example, for Lyme disease, hybrid peptides and *Borrelia* proteins, capable of binding to antibodies that are induced by *Borrelia* species infecting a subject may be used. The antibodies that recognize *Borrelia* antigens may be present in subjects that are infected with or suspected of having Lyme disease. The hybrid peptides and *Borrelia* proteins may be combined to form antigenic compositions useful for diagnosing and detecting Lyme disease in a subject or in a subject's sample. In some embodiments, the antigenic compositions may comprise a mixture of *Borrelia* antigens of at least one hybrid peptide and at least one *Borrelia* protein.

In some embodiments, the recombinant protein may include the *Borrelia* proteins listed in Table 1. It is contemplated that there may be any number of *Borrelia* proteins apart from those listed in Table 1 that are capable of eliciting an immune response indicative of the presence of *Borrelia* in a subject, and that may be suitable for use in the methods disclosed herein.

TABLE 1

Antigenic Borrelia Proteins

| ORF ID | Gene Name | MW (Dalton) |
|---|---|---|
| BB0279 | Flagellar protein FliL | 20,042 |
| BB0283 | Flagellar hook protein FlgE | 47,371 |
| BB0329 | Oligopeptide ABC transporter OppA-2 | 60,645 |
| BBA25 | Decorin binding protein B | 20,380 |
| BBG33 | BdrT (BdrF2) | 30,569 |
| BBH13 | BdrU (BdrF3) | 25,822 |
| BBK32 | Fibronectin-binding protein | 40,779 |
| BBL27 | BdrO (BdrE1) | 22,371 |
| BBM34 | BdrK (BdrD2) | 25,426 |
| BBN34 | BdrQ (BdrD10) | 20,696 |
| BBP34 | BdrA (BdrD4) | 24,100 |
| BBQ34 | BdrW (BdrE6) | 27,289 |
| BBQ42 | BdrV (BdrD5) | 20,562 |
| BB0365 | Lipoprotein LA7 | 21,848 |
| BBA36 | Hypothetical protein | 24,181 |
| BBI42 | Hypothetical protein | 21,467 |
| BBN27 | BdrR (BdrE2) | 22,244 |

TABLE 1-continued

Antigenic Borrelia Proteins

| ORF ID | Gene Name | MW (Dalton) |
|---|---|---|
| BBM27 | RevA | 17,903 |
| BBP39 | ErpB | 43,618 |
| BBQ03 | Hypothetical protein | 21,320 |
| BBN38 | ErpP (CRASP-3) | 20,671 |
| BBO34 | BdrM (BdrD3) | 21,956 |
| BBA64 | Hypothetical protein | 34,916 |
| BB0147 | Flagellar filament (FlaB) | 35,747 |

Additional non-limiting examples of *Borrelia* proteins that may be used herein include BBK07 (Hypothetical protein), OspA, OspA substrate binding protein, OspB, OspC, OspC-derived peptide (pepC10), OspD, VlsE, VlsE-derived C6, BmpA, p18, p21, p37, p39, p66, p83, an immunodominant protoplasmic cylinder antigen associated with the flagellum, and immunogenic integral membrane lipoproteins.

In some embodiments, the hybrid peptides may comprise different combinations of individual peptides and antigenic portions of larger peptides combined together. For example, the following sequences are from hybrid peptides made from antigenic proteins including, but not limited to, BBK07, BBA25, BB0147, BBA64, BB0283, OspA substrate binding protein, OspC-derived peptide (pepC10), VlsE-derived C6: SEQ ID NO:1 (CMKKDDQIAAAMVLRGMAKDGQFALKKWHVDN-PIDEATAPVVAESPKKP), SEQ ID NO:2 (CMKKDDQIAAAIALRGMAKDGKFAVKELTSPV-VAESPKKP), SEQ ID NO:3 (CMKKDDQIAAAMVLRG-MAKDGQFALKPVVAESPKKP), SEQ ID NO:4 (CPV-VAESPKKPMKKDDQIAAAMVLRGMAKDGQFALK), SEQ ID NO:5 (CMKKDDQIAAAIALRGMAKDGK-FAVKELTSPVVAESPKKPITKLTPEELENLAK), SEQ ID NO:6 (CMKKDDQIAAAIALRGMAKDGKFAVKELTSPV-VAESPKKPMKKDDQIAAAMVLRGMA KDGQ-FALKPVVAESPKKP). In some embodiments, the hybrid peptides may be made from 2 or more, 3 or more, 4 or more, 5 or more, etc., antigenic peptides or fragments thereof.

In some embodiments, the hybrid peptides used herein may comprise or consist of an amino acid sequence of SEQ ID NO:1, or the functionally equivalent sequences thereof. In some embodiments, the hybrid peptides used herein may comprise or consist of an amino acid sequence of SEQ ID NO:2, or the functionally equivalent sequences thereof. In some embodiments, the hybrid peptides used herein may comprise or consist of an amino acid sequence of SEQ ID NO:3, or the functionally equivalent sequences thereof. In some embodiments, the hybrid peptides used herein may comprise or consist of an amino acid sequence of SEQ ID NO:4, or the functionally equivalent sequences thereof. In some embodiments, the hybrid peptides used herein may comprise or consist of an amino acid sequence of SEQ ID NO:5, or the functionally equivalent sequences thereof. In some embodiments, the hybrid peptides used herein may comprise or consist of an amino acid sequence of SEQ ID NO:6, or the functionally equivalent sequences thereof. A functionally equivalent sequence refers to a sequence that is homologous in function, and varies in sequence by one or several amino acids from the original sequence with other molecular forms of the amino acids, non-natural amino acids and/or derivatives, as long as the three-dimensional structure of the original sequence is mimicked.

In some embodiments, the hybrid peptides may be hybrid peptides having a combination of two or more antigenic amino acid sequences. For example, SEQ ID NO:1 is a hybrid peptide containing highly immunogenic sequences from three *Borrelia* antigens, OspC, VlsE(C6-Vmp) and BBK07. It is contemplated that different amino acid sequences may be combined using any number of known cross-linking reagents. Other methods of combining the amino acid sequences known to those of skill in the art may also be used. The substitutions of the amino acid sequences may be introduced as long as the change does not interfere with the binding of the antibodies.

It is contemplated that in some embodiments each of the at least three capture moieties may comprise an antigenic composition which is made up of different combinations of hybrid peptides and *Borrelia* proteins within a mixture. Non-limiting examples of different combinations include a mixture of one hybrid peptide and two *Borrelia* proteins, a mixture of one hybrid peptide and three *Borrelia* proteins, a mixture of two hybrid peptides and one *Borrelia* protein, a mixture of two hybrid peptides and two *Borrelia* proteins, a mixture of two hybrid peptides and three *Borrelia* proteins, a mixture of at least two hybrid peptides and at least three *Borrelia* proteins, or a mixture of all hybrid peptides. In some embodiments, an antigenic composition may comprise at least one hybrid peptide. In some embodiments, an antigenic composition may comprise at least one *Borrelia* protein. In some embodiments, an antigenic composition may comprise a mixture of BBA25, BB0147, and an amino acid sequence of SEQ ID NO:1.

As stated, each of the at least three capture moieties may include a solid support and an antigen of the disease-causing agent. Suitable solid supports or carriers include, but are not limited to, glass surfaces (e.g., a glass slide or bead), plastic surfaces, metal surfaces, polystyrene surfaces (e.g., a bead or a plate), nitrocellulose surfaces, microparticles, nanoparticle surfaces, a flow path in a lateral flow assay device, a flow path in a microfluidic cassette, a well in a microtiter plate, wells, disposable ECL electrodes, and superparamagnetic, paramagnetic, or magnetic particles or beads that may be coated with avidin or streptavidin or have other surface functionalities to promote binding affinity.

In some embodiments, the assay components described herein may be linked or bound to various constituents or moieties in order to perform assay functions. For example, in some embodiments, the assay components and the antigens discussed herein may be bound directly through covalent or non-covalent attachment, or indirectly to a solid support or carrier. When bound indirectly, intermediate linkers may be used to bind the components. Non-limiting examples of suitable intermediate linkers include an amino group or a carboxylate group, biotin, ligands, or other chemical bonds.

As stated, the detection moiety may include a binding partner attached to a label. In some embodiments, the detection moiety may comprise any label that corresponds to a suitable detection method. Non-limiting examples of suitable labels include electrochemiluminescence labels or compounds, chemiluminescent compounds, enzyme labels, fluorophores, chromogenic compounds, radiolabels, catalysts, colorimetric compounds or labels, labeled antibodies, latex particle, a magnetic particle, a radioactive element, fluorescent dyes, phosphorescent dyes, dye crystalites, gold particles, silver colloidal particles, selenium colloidal particles, metal chelates, coenzymes, electro active groups, oligonucleotides or stable radicals. The metal chelate may be a ruthenium, an osmium metal chelate or a europium chelate. The detection method may include any known detection method including, but not limited to, chromogenic, radioisotopic, fluorescence, immunofluorescence, luminescence, bioluminescence, and electrochemiluminescence (ECL).

In some embodiments, the detection moiety may detect human immunoglobulin G (IgG). In other embodiments, the detection moiety may detect human immunoglobulin M (IgM).

It is contemplated that any detection system can be used to perform the methods disclosed herein. It is contemplated that the detection method may include any known detection method. Non-limiting examples of detection methods include enzyme-linked immunosorbent assays (ELISA), enzyme-based histochemical assays, chromogenic, radioisotopic, fluorescence, immunofluorescence, luminescence, bioluminescence, and electrochemiluminescence (ECL). It is to be understood that the methods disclosed herein are not limited to any particular detection system or detection moiety/label.

In some embodiments, the detecting step comprises performing an ELISA assay. In some embodiments, the detecting step comprises performing a lateral flow immunoassay. In some embodiments, the detecting step comprises performing a fluorescent assay.

In some embodiments, the detection method may be electrochemiluminescence (ECL). An electrochemiluminescent compound may serve as the label that may be detected or quantified within an ECL reaction chamber, such as in a flow cell, or on a disposable electrode. The solid support may serve to hold the complex bound to the label near an ECL electrode in the ECL reaction chamber during detection.

In some embodiments, the detecting step comprises performing an electrochemiluminescent (ECL) assay. Electrochemiluminescence (ECL) is the process whereby a molecular species, such as an "ECL label," luminesces upon the exposure of that species to electrochemical energy in an appropriate surrounding chemical environment. ECL is a rapid and sensitive bio-analytical detection technique that is a regenerative process. Some of the advantages achieved with ECL as a detection method in biological sample analysis include simpler, less expensive instrumentation; stable, nonhazardous labels; and increased assay performance characteristics such as lower detection limits, higher signal to noise ratios, and lower background levels. As a detection method in clinical sample analysis, ECL also has the advantage of greater sensitivity and specificity. Certain applications of ECL have been developed and reported in the literature. U.S. Pat. Nos. 5,147,806, 5,068,808, 5,061,445, 5,296,191, 5,247,243, 5,221,605, 5,238,808, 5,310,687, 5,714,089, 6,165,729, 6,316,607, 6,808,939, 6,881,589, 6,881,536, and 7,553,448, the disclosures of which are incorporated herein by reference, detail certain methods, apparatuses, chemical moieties, inventions, and associated advantages of ECL.

Electrochemiluminescence signals are generated by a redox reaction between an electrochemiluminescent label such as an ECL-active label with a redox substrate that occurs at the surface of an electrode. In certain embodiments, the ECL label is a ruthenium(Ru)-containing reagent. One example of a suitable electrochemiluminescent label is Tris(bipyridine)ruthenium(II) ($[Ru(bipy)3]^{2}+$), also referred to as TAG. In some embodiments, the redox substrate is tripropylamine (TPA).

In some embodiments, a magnet usually positioned below an electrode may attract the magnetic beads, pulling down the Ru-labeled complex near the electrode. In some embodiments, the ECL reaction can occur in an ECL analyzer. The Ru may then be oxidized. Oxidized tripropylamine (TPA) may react with the oxidized Ru, which then may emit a photon. The redox reaction between Ru and the redox substrate tripropylamine (TPA) that occurs only in the electric field near the electrode may be a regenerative process during continued application of voltage, which allows for an ECL signal that undergoes amplification over time. Because photons can only be generated near the electrode surface, electrochemiluminescence only occurs when the Ru is brought into proximity with the electrode by the magnet, thereby reducing background levels. Nonspecific ECL is not triggered by any known natural constituents of biological samples; therefore, unlike chemiluminescence, which often displays background artifacts due to nonspecific triggering of chemiluminescent detection moieties, ECL maintains reduced background levels.

In some embodiments, the capture moiety and/or the detection moiety may be from a lyophilized composition that is rehydrated with the sample for use in an assay. In some embodiments, the lyophilized composition may contain standard and/or other necessary assay-specific components of an assay, such as buffers, reagents, detergents, preservatives, salts, proteins, antibodies, etc. It is contemplated that the capture moiety and the detection moiety may be lyophilized in separate compositions, and then rehydrated with the sample. It is also contemplated that the capture moiety and the detection moiety may be lyophilized in the same composition, and then rehydrated with any of the buffer, pretreatment solution or the sample. A multi-step rehydration is also contemplated, where two or more lyophilized compositions are rehydrated in separate steps.

In some embodiments, the *Borrelia* antigen is from an infectious *Borrelia* species, such as *Borrelia afzelii, Borrelia burgdorferi, Borrelia garinii, Borrelia miyamotoi* and *Borrelia valaisiana*. It is contemplated that other species of *Borrelia* that have been implicated in Lyme disease can also be detected using the methods described herein, so long as those species induce antibodies that can react specifically with the hybrid peptides and/or *Borrelia* proteins disclosed herein.

In some embodiments, the hybrid peptides and *Borrelia* proteins described herein may be combined with a sample to perform the assays. The sample may be from a subject including, but not limited to, a human, a canine or an equine subject. The sample may be a biological sample, such as tissue extracts, tissues used in immunohistochemistry, or fluids. The fluid samples may be derived from blood, plasma, serum, cerebrospinal fluid, synovial fluid, aqueous tumor, ascites fluid, saliva, sputum, urine or other bodily fluids.

It is contemplated that the steps of the methods of the present disclosure do not have to be completed in the order provided herein, and may be performed in different orders, where, for example, the detection moiety and the composition described herein, may be added to or contacted with the sample sequentially or at the same time.

If the capture moieties and detection moieties are added sequentially, it is contemplated that the sample may be incubated for a period of time after the addition of each assay component and before the next method step(s). Additionally, the sample may be incubated for a period of time before the washing step and removal of any unbound or excess materials. It is further contemplated that additional washing steps to remove materials during the assay may be performed at additional times during the method, such as after the addition of each assay component, after the addition of both assay components together and/or before the detecting step.

In certain aspects of the present disclosure, methods for detecting antibodies to Lyme disease in a sample from a subject suspected of having Lyme disease comprise contacting the sample with three capture moieties and a detection moiety; and detecting a signal from the detection moiety, wherein the three capture moieties comprise BBA25 (Decorin binding protein B), BB0147 (Flagellar filament (FlaB)), and a hybrid peptide comprising an amino acid sequence of SEQ ID NO:1, and each are capable of forming at least one complex with at least one antibody to a *Borrelia* antigen in the sample, wherein the detection moiety binds to the antibody of the antibody-capture moiety complex. The formation of the at least one complex is indicative of the presence of a Lyme antibody to the *Borrelia* antigen in the sample. The amount of signal detected is directly proportional to the anti-Lyme antibody in the sample.

In certain aspects of the present disclosure, methods for detecting an antibody to a *Borrelia* antigen in a sample, comprise contacting a sample with a mixture of hybrid peptides and *Borrelia* proteins, such as those disclosed herein, and detecting an antibody of an antibody-antigen complex with a detection moiety, wherein formation of the antibody-antigen complex is indicative of the presence of an antibody to a *Borrelia* antigen in the sample. The amount of signal detected is directly proportional to the antibody to the *Borrelia* antigen in the sample. As stated, the presence of a *Borrelia* antigen in the sample indicates that the subject's immune system has made the antibodies in response to a *Borrelia* infection.

In other aspects of the present disclosure, methods for diagnosis of Lyme disease in a sample from a subject suspected of having Lyme disease, are disclosed, comprising contacting a sample with a mixture of antigens disclosed herein and a detection moiety, the mixture capable of forming an antibody-antigen complex, and detecting the presence of an antibody of the antibody-antigen complex, wherein the detection of the antibody is indicative of the subject having Lyme disease.

Kits

Another aspect of the present disclosure is directed to kits using the compositions described herein and for performing the methods described herein. For example, a kit may be used for detecting anti-*Borrelia* antibodies in a sample or for diagnosing Lyme disease in a subject. Materials to be included in the kit may vary depending on the ultimate purpose. As such, the kits may include one or more components that are used in the methods disclosed herein. The kits disclosed herein may include at least one component selected from the following components: at least one antigen, at least one hybrid peptide, at least one *Borrelia* protein, at least one capture moiety, a labeled component, a binding partner attached to a detection moiety or a detector antibody attached to a detection moiety, a detection moiety, a solid support, a pretreatment formulation, necessary assay buffers and reagents, standards and/or controls and instructions for performing the methods disclosed herein, as well as other components and elements of the methods described herein. The standards and/or controls can be additional chemical reagents or data (empirical) in printed or electronic form necessary for the calibration needed for performance of the assay. The kit may also include the use of a portable ECL analyzer instrument, including instructions for use and related instrument components, such as cartridges used with the analyzer instrument.

The present disclosure can be better understood by reference to the examples included herein, which illustrate but do not limit the present teachings described herein. It is to be understood that both the descriptions disclosed herein and the following examples are merely illustrative and intended to be non-limiting.

EXAMPLES

Specific examples of the invention are illustrated and/or described herein. However, it will be appreciated that modifications and variations of the invention are covered by the above teachings and within the purview of the claims without departing from the spirit and scope of the invention.

The following examples are intended to be non-restrictive and explanatory only.

Example 1—Selection of Recombinant Proteins for ECL Lyme Assay

Twenty-four (24) recombinant Lyme proteins listed in Table 1 were commercially produced using standard recombinant protein production and purification procedures. The gene sequences for those proteins listed in Table 1 were based on the published genome for *Borrelia burgdorferi* B31 lab strain. Each construct contained a six (6) Histidine amino acid tag sequence on its C-terminal end for use in protein detection and purification.

A screening assay was performed to select the proteins appropriate for use in an assay. The screening assay included a set of commercially available known Lyme-positive (i.e., containing anti-Lyme antibody) plasma samples. Each sample was pre-treated with a $F(ab')_2$ fragment that recognized Fc regions of IgG (250 μg/mL) or IgM (25 μg/mL). Each antigen was biotinylated. The biotinylated antigens were pre-bound to streptavidin superparamagnetic particles, the combination also referred to as capture moiety, capture reagent or capture beads. Each capture bead (250 μg/mL) was analyzed independently, and two separate detector antibodies were used for identifying anti-Lyme IgG or IgM antibodies (10 μg/mL) in the plasma. The detector reagents were TAG-labeled anti-Human IgG monoclonal antibody and TAG-labeled anti-Human IgM monoclonal antibody. Upon conclusion of the assay, ECL counts were measured in an ECL analyzer. A signal/background (S/B) ratio of ≥2.0 was used as the cut-off value for positive samples. The top-performing antigen results from the screening of antigen-coated capture beads are shown in Table 2.

TABLE 2

Results from the Screening of Antigen-Coated Capture Beads

| Protein | Results (number positive/ number tested) |
|---|---|
| BB0147 | 55/56 |
| BB0283 | 46/56 |
| BBA25 | 46/56 |
| BBG33 | 41/56 |
| BB0329 | 35/56 |
| BB0279 | 31/56 |
| BBM27 | 26/56 |

Based on these data and evaluation of production and purification factors, the BB0147 and BBA25 proteins were selected for use in the ECL Lyme assay. In addition, other proteins exhibited production and purification challenges.

Example 2—Selection of Hybrid Peptides for ECL Lyme Assay

Hybrid peptides were synthesized by a commercial vendor for Wellstat Diagnostics, LLC by combining sequences from portions of immunogenic peptides, antigens and/or proteins. The hybrid peptides were tested for their ability to bind anti-Lyme antibodies in human plasma. Seven were selected for further evaluation.

The hybrid peptides were evaluated using the following experimental procedure. Capture beads containing biotinylated Lyme antigens were prepared in the assay buffer. An assay control and diluted plasma samples (1:50) were prepared in pretreatment solution (containing $F(ab')_2$ (anti-IgM) and F(ab) (anti-IgG)). 25 μL of capture beads and 25 μL of diluted sample were mixed. The capture beads and samples were incubated for 30 minutes with shaking at room temperature (RT). The plate was washed two times with 150 μL of wash solution per well. A magnet was used to retain the capture beads during washing. Working solutions of TAG-labeled anti-human IgG and IgM detection antibodies were prepared in the assay buffer. 25 μL of detector solution was added into each well and incubated for 15 minutes at room temperature. The plate was washed two times with 150 μL of wash solution per well. A magnet was used to retain the capture beads during washing. The capture beads with antibody-antigen complexes were resuspended in 100 μL of WD Wash Solution. An ECL analyzer with 50 μL read volume was used to read results.

The results are provided in FIGS. 1 and 2. The S/B ratio >2 indicated a positive result (shaded). "Confirmed*" indicates a sample that was positive in Lyme disease two-tier testing performed by the vendor. ECL counts represent the mean of samples run in duplicate. The pooled normal counts are considered background for each capture bead.

Selected normal and Lyme-positive plasma samples from a commercially available panel of mixed Lyme samples were analyzed with six hybrid peptide capture beads using IgG and IgM detectors. The confirmed Lyme IgG positive samples all yielded positive results as expected with each of the six capture bead types (See FIG. 1). The confirmed Lyme IgM positive samples all yielded positive results as expected with each of the six capture bead types (See FIG. 2).

Negative plasma sample PTL-202-9 showed a negative result in three hybrid peptide antigens, HP-NL-P1, HP-NL-1, and HP-NL-3, with both detectors (IgG, IgM). A false positive result was shown in three hybrid peptides, HP-NL-2, HP-NL-P5 and $HP-[VO]_2$ with the IgG detector.

Two confirmed Lyme IgM positive plasma samples (PTL-202-1, PTL-202-5) showed positive S/B ratios in all six beads with IgM detector. One IgG-confirmed positive sample (PTL-202-3) also displayed low IgM signal with two hybrid peptides, HP-NL-3, $HP-[VO]_2$.

Overall, the best performance was demonstrated by two hybrid peptides, HP-NL-1 and HP-NL-P1. These two hybrid peptides were further evaluated and based on testing of Lyme-negative plasma, hybrid peptide HP-NL-1 had a higher false positive rate than hybrid peptide HP-NL-P1, and therefore, HP-NL-P1 was selected for use in the ECL Lyme assay (data not shown).

Example 3—Mixed Capture Reagent Evaluation

These experiments were performed to evaluate capture beads as a mixture of several antigens on streptavidin superparamagnetic particles and to confirm the best mixture in terms of the lowest occurrence of false positive and/or false negative signal.

The experimental procedure was the same as that used in Example 2 with the exception of the following: Capture beads (each coated with a different single protein) were prepared at working concentration and mixed in equal parts.

FIGS. 3 and 4 (IgG and IgM detection) provide results from the testing of different capture bead mixtures as Lyme capture reagent. In FIGS. 3 and 4, Mixture 1 represents a capture bead mix (containing 5 antigens—2 proteins and 3 antigenic sequences combined in one hybrid peptide); Mixture 2 represents one recombinant protein replaced from that in Mixture 1 (still 5 antigens); Mixture 3 represents one recombinant and one hybrid peptide replaced from Mixture 1 (4 antigens—the replacement hybrid peptide has 2 antigenic sequences); Mixture 4 represents two recombinant antigens, but not the same as in the capture mix of Mixture 1 (2 antigens); Mixture 5 represents two hybrid peptides (5 antigens), different ones than the one in the capture mix of Mixture 1; Mixture 6 represents two recombinant antigens (one recombinant used in Mixture 1); Mixture 7 represents three recombinant antigens (one recombinant used in Mixture 1); Mixture 8 represents three recombinant antigens (one recombinant used in Mixture 1).

False values are marked with an asterisk (*) and positives were S/B >2.5. Borderline/equivocal values were 2-2.4 S/B and marked with an "eq." The experiments were performed over two days.

The capture bead of Mixture 1 of FIGS. 3 and 4 performed the best (no false positive or false negative results). Other tested combinations displayed false-positive and false-negative results.

Example 4—Reproducibility of ECL Lyme Assay

The reproducibility of the Lyme assay was evaluated using clinically characterized Lyme specimens and the same Lyme assay format as used in Example 2.

The experiments were performed one run per day over 3 days.

Samples with S/B ratio >2 are considered positive. ECL counts represent the mean of samples run in duplicate. The results are provided in FIGS. 5 and 6.

The study demonstrated day-to-day reproducibility of no false signal in Lyme-negative sample and similar S/B ratio in all tested Lyme-positive samples.

Example 5—ECL Lyme Assay Performance with Clinically Characterized Human Samples from CDC Research Panel I The purpose of this experiment was to compare the ECL Lyme assay to a panel from the CDC that has been tested using the CDC two-tiered standard method. A CDC Research Lyme Panel I containing 32 samples was tested in the ECL Lyme assay (at Wellstat Diagnostics, LLC) and compared to the CDC results (determined independently). The CDC provided testing results and clinical history of each patient.

The experimental procedure for the ECL Lyme assay was the same as that used in Example 3 with the exception of the following: Three capture beads (BBA25, BB0147, HP-NL-P1) were mixed together at the ratio of 1:1:3, respectively.

S/B ratio >2.5 indicated Lyme-positive result. ECL counts represent the mean of samples run in duplicate. The sample was considered positive if any of the detectors (IgG or IgM) displayed positive results. Human samples for this example were provided by the CDC. The results are provided in FIGS. 7 and 8.

The 32 samples from the CDC Research Lyme Panel I were tested with the ECL Lyme assay. The ECL Lyme assay results from 31 samples matched the CDC two-tier results. One sample (PS58, shaded) had a positive IgM signal in the ECL Lyme assay and did not match the CDC two-tier final result. This sample was positive in the CDC first tier. The result was not confirmed by Western blot testing in the CDC second tier.

Overall, the sensitivity (as true positive rate, n=12 samples) showed 100% agreement with the CDC's two-tier final results. The specificity (as true negative rate, n=20 samples) showed 95% agreement with the CDC's two-tier final results.

Example 6—ECL Lyme Assay Performance with Clinically Characterized Human Samples from CDC Research Panel II The purpose of this experiment was to compare the ECL Lyme assay to a panel from the CDC that has been tested using the CDC two-tiered standard method. CDC Research Lyme Panel II, containing 92 blinded samples, was tested in the ECL Lyme assay and compared to the CDC results (samples provided by CDC). After the ECL Lyme assay testing was complete, the results of the ECL Lyme assay were presented to the CDC, and the samples were decoded.

The experimental procedure was the same as that used in Example 5 with the exception of the following: CDC Research Lyme Panel II was tested on an ECL analyzer which uses the same detection system as previous experiments but with upgraded hardware. This resulted in higher ECL counts and higher S/B ratio. ECL counts represent the mean of samples run in duplicate. An S/B ratio ≥15 indicated a Lyme-positive result. In the ECL Lyme assay a sample was considered positive if either of the detectors (IgG or IgM) yielded positive results. The results of the ECL Lyme assay in comparison to the data provided by CDC are presented in FIGS. 9-12. *False-positive results shaded.

The ECL Lyme assay detected 12 positive results out of 20 Early Lyme/EM patients and eight were found positive by the CDC two-tier final results (See FIG. 9).

The ECL Lyme assay detected 12 positive results out of 12 non-EM early/Late Lyme patients and 11 were found positive by the CDC two-tier final results (See FIG. 10).

Of the 24 healthy endemic and healthy non-endemic patients, all 24 were negative in the ECL Lyme assay. In the CDC first tier assay, four were determined to be false-positives and two were equivocal. However, all 24 samples were negative in the CDC two-tier final result (See FIG. 11).

Of the 36 non-Lyme patients with potentially cross-reactive diseases, 3 were false positive in the ECL Lyme assay. In the CDC first tier assay, 10 were determined to be false-positives and one was equivocal. Two were false positive in the CDC two-tier final result (See FIG. 12).

Example 7—Summary of ECL Lyme Assay Performance with Clinically Characterized Human Samples from Two CDC Research Lyme Panels I and II The data from both CDC Research Panels described in Examples 5 and 6 are summarized in FIG. 13: (−) indicates negative result, (+) indicates Lyme-positive result.

During the testing of 124 clinical samples from the CDC Research Lyme Panels I and II, the ECL Lyme assay demonstrated the following performance:

100% specificity in normal healthy subjects (from both Lyme-endemic and non-endemic areas).

Four false-positives in cross-reactive diseases (two patients with Rheumatoid Arthritis (RA), one patient with mononucleosis, one patient with fibromyalgia) compared to 18 false-positives in CDC first-tier testing and two false-positives in CDC two-tier testing (one patient with RA and one patient with syphilis).

One clinically confirmed Lyme neurologic patient was false-negative in CDC first tier and two-tier testing but tested positive by the ECL Lyme Assay.

Overall sensitivity after seroconversion (n=33) was 97% for the ECL Lyme assay and the CDC first-tier compared to 81.8% in the CDC two-tier testing.

Specificity in healthy subjects and non-Lyme patients (n=80) was 95% for ECL Lyme assay, 77.5% for CDC first-tier and 97.5% for CDC two-tier testing.

Unless otherwise expressly stated, it is in no way intended that any methods set forth herein be construed as requiring that the steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

The specification and examples disclosed herein are intended to be considered as exemplary only, with a true scope and spirit of the invention being indicated in the claims. Other embodiments of the compositions, devices and methods described herein will be apparent to those skilled in the art from consideration of the disclosure and practice of the various example embodiments disclosed herein.

Other than in the examples, or where otherwise indicated, all numbers expressing quantities of ingredients, reaction conditions, analytical measurements, and so forth used in the specification and claims are to be understood as being modified in all instances by the term “about.” Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

As used herein the terms “the,” “a,” or “an” mean “at least one,” and should not be limited to “only one” unless explicitly indicated to the contrary. Thus, for example, “a hybrid peptide” should be construed to mean “at least one hybrid peptide.”

All publications, patents and patent applications mentioned in this specification are herein incorporated by reference in their entirety into the specification to the same extent as if each individual publication, patent or patent application was specifically and individually indicated to be incorporated herein by reference.

What is claimed is:

1. A method of detecting antibodies to Lyme disease in a sample from a subject suspected of having Lyme disease, the method comprising:

contacting the sample with three capture moieties and a detection moiety; and detecting a signal from the detection moiety, wherein one of the three capture moieties is a BBA25 (Decorin binding protein B) protein attached to a solid support, one is a BB0147 (Flagellar filament (FlaB)) protein attached to a solid support, and one is a hybrid peptide consisting of amino acid sequence SEQ ID NO:1 attached to a solid support, and each is capable of forming at least one complex with at least one antibody to a *Borrelia* antigen in the sample, wherein the detection moiety binds to the antibody of the antibody-capture moiety complex, wherein the formation of the at least one complex is indicative of the presence of an anti-Lyme antibody to the *Borrelia* antigen in the sample, and wherein the amount of signal detected is proportional to the anti-Lyme antibody in the sample.

2. The method of claim 1, wherein the detection moiety is capable of detecting immunoglobulin G (IgG).

3. The method of claim 1, wherein the detection moiety is capable of detecting immunoglobulin M (IgM).

4. The method of claim 1, wherein the detection moiety comprises a binding partner and a label, and wherein the label is selected from the group consisting of electrochemiluminescence labels or compounds, chemiluminescent compounds, enzyme labels, fluorophores, chromogenic compounds, radiolabels, catalysts, colorimetric, labeled antibodies a latex particle, a magnetic particle, a radioactive element, fluorescent dyes, phosphorescent dyes, dye crystalites, gold particles, silver colloidal particles, selenium colloidal particles, metal chelates, coenzymes, electro active groups, oligonucleotides, and stable radicals.

5. The method of claim 4, wherein the metal chelate comprises a ruthenium or an osmium metal chelate.

6. The method of claim 1, wherein the *Borrelia* antigen comprises an antigen from a *Borrelia afzelii, Borrelia burgdotieri, Borrelia garinii, Borrelia miyamotoi*, or *Borrelia valaisiana* species.

7. The method of claim 1, wherein the solid support comprises a bead, a superparamagnetic bead, a paramagnetic bead, a plate, a glass surface, a plastic surface, a metal surface, a polystyrene surface, a nitrocellulose surface, a microparticle, a nano-particle surface, a flow path in a lateral flow assay device, or a well in a microtiter plate.

8. The method of claim 1, wherein the detecting step comprises performing an ELISA assay, a lateral flow assay, a fluorescence assay, or an electrochemiluminescence assay.

9. The method of claim 1, wherein the detecting step comprises performing an electrochemiluminescence assay.

10. The method of claim 1, wherein the sample comprises a human sample, a canine sample, or an equine sample.

11. The method of claim 1, wherein the sample comprises a blood, a serum, a plasma, a cerebrospinal fluid, a urine, or a saliva sample.

* * * * *

SEQUENCE LISTING

```
<160> NUMBER OF SEQ ID NOS: 8

<210> SEQ ID NO 1
<211> LENGTH: 49
<212> TYPE: PRT
<213> ORGANISM: Borrelia

<400> SEQUENCE: 1

Cys Met Lys Lys Asp Asp Gln Ile Ala Ala Ala Met Val Leu Arg Gly
1               5                   10                  15

Met Ala Lys Asp Gly Gln Phe Ala Leu Lys Lys Trp His Val Asp Asn
            20                  25                  30

Pro Ile Asp Glu Ala Thr Ala Pro Val Val Ala Glu Ser Pro Lys Lys
        35                  40                  45

Pro


<210> SEQ ID NO 2
<211> LENGTH: 40
<212> TYPE: PRT
<213> ORGANISM: Borrelia

<400> SEQUENCE: 2

Cys Met Lys Lys Asp Asp Gln Ile Ala Ala Ala Ile Ala Leu Arg Gly
1               5                   10                  15

Met Ala Lys Asp Gly Lys Phe Ala Val Lys Glu Leu Thr Ser Pro Val
            20                  25                  30

Val Ala Glu Ser Pro Lys Lys Pro
```

```
        35                  40


<210> SEQ ID NO 3
<211> LENGTH: 36
<212> TYPE: PRT
<213> ORGANISM: Borrelia

<400> SEQUENCE: 3

Cys Met Lys Lys Asp Asp Gln Ile Ala Ala Ala Met Val Leu Arg Gly
1               5                   10                  15

Met Ala Lys Asp Gly Gln Phe Ala Leu Lys Pro Val Val Ala Glu Ser
            20                  25                  30

Pro Lys Lys Pro
        35


<210> SEQ ID NO 4
<211> LENGTH: 36
<212> TYPE: PRT
<213> ORGANISM: Borrelia

<400> SEQUENCE: 4

Cys Pro Val Val Ala Glu Ser Pro Lys Lys Pro Met Lys Lys Asp Asp
1               5                   10                  15

Gln Ile Ala Ala Ala Met Val Leu Arg Gly Met Ala Lys Asp Gly Gln
            20                  25                  30

Phe Ala Leu Lys
        35


<210> SEQ ID NO 5
<211> LENGTH: 54
<212> TYPE: PRT
<213> ORGANISM: Borrelia

<400> SEQUENCE: 5

Cys Met Lys Lys Asp Asp Gln Ile Ala Ala Ala Ile Ala Leu Arg Gly
1               5                   10                  15

Met Ala Lys Asp Gly Lys Phe Ala Val Lys Glu Leu Thr Ser Pro Val
            20                  25                  30

Val Ala Glu Ser Pro Lys Lys Pro Ile Thr Lys Leu Thr Pro Glu Glu
        35                  40                  45

Leu Glu Asn Leu Ala Lys
    50


<210> SEQ ID NO 6
<211> LENGTH: 75
<212> TYPE: PRT
<213> ORGANISM: Borrelia

<400> SEQUENCE: 6

Cys Met Lys Lys Asp Asp Gln Ile Ala Ala Ala Ile Ala Leu Arg Gly
1               5                   10                  15

Met Ala Lys Asp Gly Lys Phe Ala Val Lys Glu Leu Thr Ser Pro Val
            20                  25                  30

Val Ala Glu Ser Pro Lys Lys Pro Met Lys Lys Asp Asp Gln Ile Ala
        35                  40                  45

Ala Ala Met Val Leu Arg Gly Met Ala Lys Asp Gly Gln Phe Ala Leu
    50                  55                  60

Lys Pro Val Val Ala Glu Ser Pro Lys Lys Pro
65                  70                  75
```

<210> SEQ ID NO 7
<211> LENGTH: 157
<212> TYPE: PRT
<213> ORGANISM: Borrelia

<400> SEQUENCE: 7

Met Ala Leu Glu Ser Ser Ser Lys Asp Leu Lys Asn Lys Ile Leu Lys
1 5 10 15

Ile Lys Lys Glu Ala Thr Gly Lys Gly Val Leu Phe Glu Ala Phe Thr
20 25 30

Gly Leu Lys Thr Gly Ser Lys Val Thr Ser Gly Gly Leu Ala Leu Arg
35 40 45

Glu Ala Lys Val Gln Ala Ile Val Glu Thr Gly Lys Phe Leu Lys Ile
50 55 60

Ile Glu Glu Glu Ala Leu Lys Leu Lys Glu Thr Gly Asn Ser Gly Gln
65 70 75 80

Phe Leu Ala Met Phe Asp Leu Met Leu Glu Val Val Glu Ser Leu Glu
85 90 95

Asp Val Gly Ile Ile Gly Leu Lys Ala Arg Val Leu Glu Glu Ser Lys
100 105 110

Asn Asn Pro Ile Asn Thr Ala Glu Arg Leu Leu Ala Ala Lys Ala Gln
115 120 125

Ile Glu Asn Gln Leu Lys Val Val Lys Glu Lys Gln Asn Ile Glu Asn
130 135 140

Gly Gly Glu Lys Lys Asn Asn Lys Ser Lys Lys Lys Lys
145 150 155

<210> SEQ ID NO 8
<211> LENGTH: 336
<212> TYPE: PRT
<213> ORGANISM: Borrelia

<400> SEQUENCE: 8

Met Ile Ile Asn His Asn Thr Ser Ala Ile Asn Ala Ser Arg Asn Asn
1 5 10 15

Gly Ile Asn Ala Ala Asn Leu Ser Lys Thr Gln Glu Lys Leu Ser Ser
20 25 30

Gly Tyr Arg Ile Asn Arg Ala Ser Asp Asp Ala Ala Gly Met Gly Val
35 40 45

Ser Gly Lys Ile Asn Ala Gln Ile Arg Gly Leu Ser Gln Ala Ser Arg
50 55 60

Asn Thr Ser Lys Ala Ile Asn Phe Ile Gln Thr Thr Glu Gly Asn Leu
65 70 75 80

Asn Glu Val Glu Lys Val Leu Val Arg Met Lys Glu Leu Ala Val Gln
85 90 95

Ser Gly Asn Gly Thr Tyr Ser Asp Ala Asp Arg Gly Ser Ile Gln Ile
100 105 110

Glu Ile Glu Gln Leu Thr Asp Glu Ile Asn Arg Ile Ala Asp Gln Ala
115 120 125

Gln Tyr Asn Gln Met His Met Leu Ser Asn Lys Ser Ala Ser Gln Asn
130 135 140

Val Arg Thr Ala Glu Glu Leu Gly Met Gln Pro Ala Lys Ile Asn Thr
145 150 155 160

Pro Ala Ser Leu Ser Gly Ser Gln Ala Ser Trp Thr Leu Arg Val His
165 170 175

-continued

```
Val Gly Ala Asn Gln Asp Glu Ala Ile Ala Val Asn Ile Tyr Ala Ala
            180                 185                 190

Asn Val Ala Asn Leu Phe Ser Gly Glu Gly Ala Gln Thr Ala Gln Ala
        195                 200                 205

Ala Pro Val Gln Glu Gly Val Gln Gln Glu Gly Ala Gln Gln Pro Ala
    210                 215                 220

Pro Ala Thr Ala Pro Ser Gln Gly Gly Val Asn Ser Pro Val Asn Val
225                 230                 235                 240

Thr Thr Thr Val Asp Ala Asn Thr Ser Leu Ala Lys Ile Glu Asn Ala
                245                 250                 255

Ile Arg Met Ile Ser Asp Gln Arg Ala Asn Leu Gly Ala Phe Gln Asn
            260                 265                 270

Arg Leu Glu Ser Ile Lys Asn Ser Thr Glu Tyr Ala Ile Glu Asn Leu
        275                 280                 285

Lys Ala Ser Tyr Ala Gln Ile Lys Asp Ala Thr Met Thr Asp Glu Val
    290                 295                 300

Val Ala Ala Thr Thr Asn Ser Ile Leu Thr Gln Ser Ala Met Ala Met
305                 310                 315                 320

Ile Ala Gln Ala Asn Gln Val Pro Gln Tyr Val Leu Ser Leu Leu Arg
                325                 330                 335
```